United States Patent [19]
Martin et al.

[11] Patent Number: 5,891,648
[45] Date of Patent: Apr. 6, 1999

[54] REACTION-BASED SELECTION FOR EXPRESSION OF AND CONCENTRATION OF CATALYTIC MOIETIES

[75] Inventors: Mark T. Martin, Germantown; Rodger G. Smith, Jefferson; Michael J. Darsley, Rockville; David M. Simpson, Adelphi; Gary F. Blackburn, Gaithersburg, all of Md.

[73] Assignee: Igen, Inc., Gaithersburg, Md.

[21] Appl. No.: 748,415

[22] Filed: Nov. 13, 1996

Related U.S. Application Data

[62] Division of Ser. No. 377,495, Jan. 24, 1995, Pat. No. 5,631,137, which is a continuation of Ser. No. 250,934, May 31, 1994, abandoned, which is a continuation of Ser. No. 101,274, Aug. 2, 1993, abandoned, which is a continuation of Ser. No. 841,648, Feb. 24, 1992, abandoned.

[51] Int. Cl.$^6$ ........................................ C12Q 1/25
[52] U.S. Cl. .................. 435/7.6; 435/7.4; 435/188.5
[58] Field of Search ...................... 435/7.6, 7.4, 188.5

[56] References Cited

PUBLICATIONS

Barbas III et al., *Assembly of Combinatorial Antibody Liebraires on Phage Surfaces: the Gene III Site*, Proc. Natl. Acad. Sci., USA (1991) 88; 7978–82.

Clackson, T., et al., *Making antibody fragments using phage display libraries*, Nature (1991), vol. 352 pp. 624–628.

Henis et al., "Mobility of Enzymes on Insoluable Substrates" the β–Amylase–Starch Gel System, Biopolymers, vol. 27 pp. 123–138 (1988).

Henis, Y.I., et al. (1988) *Chem. Abstracts*, 108:127440x.

Huse, W. et al., *Generation of a Large Combinatorial Library of the Immunoglobulin Repertoire in Phage Lambda*, Science, vol. 246, (Dec. 1989), pp. 1275–1284.

Katchalski–Katzir et al., *Enzyme Diffusion and Action on Soluble and Insoluble Substrate Biopolymers*, Biopolymers, vol. 24. pp. 257–276 (1985).

Katchalski–Katzir, et al., (1985) *Chem. Abstracts*, 102:145236r.

McCafferty, et al., *Phage antibodies: filamentous phage displaying antibody Variable domains*, Nature (1990) 348 552–554.

Richter, P.H. and Eigen, M., *Diffusion Controlled Reaction. Rates in Spheroidal–Geometry. Application to Repressor––Operator Association and Membrane Bound Enzymes*, Biophysical Chemistry 2 (1974) 255–263.

Richter, P.H., et al., (1974) *Chem. Abstracts*, 53051s.

Boder, E. T., et al. (1997) Nature Biotechnology 15, 553–5.57.

Kieke, M. C., et al. (1997) Protein Engineering 10(11), 1303–1310.

Georgiou, G., et al. (1997) Nature Biotechnology 15, 29–34.

*Primary Examiner*—Charles L. Patterson, Jr.
*Attorney, Agent, or Firm*—Whitman Breed Abbott & Morgan LLP

[57] ABSTRACT

Disclosed and claimed are methods for selecting a recombinant virus, phage or cell expressing a catalytic antibody or catalytic portion thereof, or for selecting catalytic activity by a moiety. The method employs reaction-based selection for catalytic activity. The method can also be used to concentrate (increase the proportion of catalytic to non-catalytic moieties) a sample containing a catalytic moiety or viruses, phages or cells expressing a catalytic moiety. The selection or concentrating can be by employing a mechanism-based inhibitor, catalysis-accelerated movement, surface binding, changes in enthalpic component of binding as a function of temperature, or changes in binding by competition, or combinations thereof. The invention also comprehends a method for producing a recombinant virus or a cell-line expressing a catalytic moiety such as a catalytic antibody or catalytic portion thereof; and, this method can include infecting a suitable host with viruses which are screened for the expression. In addition, recombinant viruses and cell-lines so expressing a catalytic moiety such as a catalytic antibody or catalytic portion thereof are also disclosed and claimed.

4 Claims, 2 Drawing Sheets

REACTION-BASED SELECTION FOR EXPRESSION OF AND CONCENTRATION OF CATALYTIC MOIETIES

This application is a division of U.S. application Ser. No. 08/377,495, filed Jan. 24, 1995 and now issued on May 20, 1997 as U.S. Pat. No. 5,631,137, which is a continuation of U.S. application Ser. No. 08/250,934, filed May 31, 1994, now abandoned, which is a continuation of U.S. application Ser. No. 08/101,274, filed Aug. 2, 1993 and now abandoned, which is a continuation of U.S. application Ser. No. 07/841,648 filed Feb. 24, 1992 and now abandoned.

FIELD OF THE INVENTION

This invention broadly relates to methods for selection for catalytic moieties, to methods for increasing the concentration of catalytic moieties in a sample containing catalytic moieties, and to substantially pure or concentrated catalytic products from such methods. This invention also relates to methods for selection or concentrating a population of recombinant viruses suspected of including viruses expressing catalytic antibodies or catalytic portions thereof. This invention also relates to detecting recombinant viruses that express a catalytic antibody or catalytic portions thereof and act catalytically. This invention further relates to a method for producing a recombinant virus or a cell-line expressing a catalytic antibody or catalytic portions thereof by infecting a host susceptible to infection by a recombinant virus that expresses a catalytic antibody or catalytic portion thereof. This invention also relates to substantially pure recombinant virus or cell populations which express a catalytic antibody or catalytic portion thereof from the aforesaid methods.

BACKGROUND OF THE INVENTION

Throughout this disclosure reference will be made to the published literature by numerals in parenthesis. These numerical references correspond to a listing of such literature references appearing at the end of this disclosure; all of these literature references being hereby incorporated herein by reference.

Viruses infect cells and divert the biosynthetic apparatus of the cell to synthesizing virus progeny. Certain viruses infect the host cell, cause the host DNA to break down and virus progeny to form in the cell whereupon the cell lyses with the release of mature virus progeny. Other viruses are lysogenic. These viruses infect a host cell and the viral DNA becomes inserted into a region of the host chromosome whereupon for generations the resultant cell-line (from replication of the infected cell) expresses genetic products of the virus. A progeny of the original infected cell can spontaneously release the viral DNA from its chromosome or be induced to do the same, whereupon a lytic cycle resulting in viral progeny occurs. An example of this latter type of virus is the phage lambda which on certain occasions, e.g., exposure to certain chemicals or radiation such as ultraviolet light, may initiate a lytic cycle immediately after infection but can otherwise exist as a provirus or prophage in the *E. coli* host genome for many generations.

A recent development in the field of antibodies is the amplification by the polymerase chain reaction (PCR) of nucleotide sequences for antibodies or portions thereof (1). An extension of this development is the insertion of these sequences into the genome of viruses, especially phages or bacteriophages (2, 3, 4, 11). In this regard reference is expressly made to PCT Patent Publication WO920 1047, published Jan. 23, 1992 entitled "Methods For Producing Members of Specific Binding Pairs," incorporated herein by reference. Likewise, the expression of a catalytically-active enzyme on the surface of a phage has been achieved (32).

For instance, Clackson et al. (2) report using a random combinational library of rearranged sequences for heavy ($V_h$) and kappa ($V_k$) light chains from mice immune to the hapten 2-phenyloxazol-5-one (phOx) to display diverse libraries of antibody fragments on the surface of the fd phage. The recombinant fd phages were selected by passing the population thereof over an affinity column.

Likewise, McCafferty et al. (3) report that complete antibody V domains can be displayed on the surface of a recombinant fd bacteriophage and that those that bind to an antigen (e.g., one in a million) can be isolated by affinity chromatography. And, McCafferty et al. (32) report the expression and affinity chromatography of functional alkaline phosphatase on the surface of a bacteriophage.

Similarly, Huse et al. (4) relate employing the bacteriophage lambda vector system to express in *E. coli* a combinatorial library of Fab fragments. Selection for expression was by selection for binding to an antigen.

A problem with the technique of selection of recombinant phages suspected of expressing catalytic antibodies or catalytically active portions thereof by hapten or antigen binding or affinity is that initially an enormous number of phages are produced; for instance, of the order of greater than $10^5$. Selection for hapten-binding from this enormous population of phages still yields an enormous subpopulation of phages (that bind); for instance, of the order of 6,000–10,000 phages. However, in this first subpopulation that bind there is yet a smaller second subpopulation that not only express the antibody on their surface (and therefore bind to the hapten), but, also display a catalytic antibody (i.e., the antibody or portion thereof expressed is catalytic). Thus, isolation of only the first subpopulation (that bind with the antigen or hapten) does not adequately screen the recombinant phage population to isolate those members which express the antibody or portion thereof catalytically. That is, hapten-binding selection is insufficient: to isolate those members of the recombinant phage population which express catalytic antibodies or portions thereof for further use; e.g., for infecting a host cell such as *E. coli* and producing consistent generations of recombinant phage or cells expressing the catalytic antibody or a catalytic portion thereof. Indeed, in a broader scope, a problem facing the development of catalysts such as catalytic antibodies, is the inability to economically enrich or select for moieties, e.g., antibodies, exhibiting the desired catalytic activity from among a vast excess of non-catalytic moieties, e.g., a vast excess of non-catalytic antibodies raised against the same transition state analogs.

Further, prior methods for selection of catalytic activity of antibody fragments (as opposed to their identification through extensive selection exercises) depends on biological selection based on the ability to compliment genetic defect in an organism expressing the fragment (16).

Heretofore there has been no method for selection of recombinant viruses or cells infected by such viruses displaying catalytic antibodies or catalytic portions thereof based upon catalytic properties of such viruses or cells.

In the area of enzymology the literature (5, 6) reports reactants called mechanism-based inhibitors (affinity labels or suicide substrates). These reactants bind in the active site of an enzyme as normal substrates do, but, contrary to normal substrates, exploit the chemical features of the reaction mechanism to form an irreversible adduct with the enzyme. Such reactants have been specifically designed for many enzymes and enzyme mechanisms. Generally, a nucleophilic enzyme amino acid residue that participates in the normal substrate catalytic reaction reacts instead with the mechanism-based inhibitor and is permanently inactivated. Haptens which were suicide substrates have been used to elicit antibodies (14). The suicide substrates were not used for selection of antibodies having catalytic activity.

Thus, heretofore there has been no application of mechanism-based inhibitors to select recombinant phage or recombinant phage infected cell populations for members expressing a catalytic antibody or catalytic portion thereof or to increase the concentration of members expressing catalytic moieties. Nor has there been any application of mechanism-based inhibitors to screen for catalytic moieties, such as catalytic moieties expressed by phages, cells, or other self-replicating systems, or catalytic peptides, oligopeptides, polypeptides, or enzymes. Nor has there been any application of mechanism-based inhibitors to increase the concentration of catalytic moieties in a sample containing catalytic moieties.

Work with enzymes show that active enzymes can "crawl" across a two-dimensional surface covered with substrate (on a micrometer distance scale), while inactive enzymes with the same binding affinity for the substrate are greatly restricted in their mobility (7, 8, 9). However, heretofore there has been no application of a two dimensional surface including a substrate of a desired catalytic reaction for selection of recombinant phage or recombinant phage infected cell population for members expressing a catalytic antibody or catalytic portion thereof or to increase the concentration of members expressing catalytic moieties. Nor has there been any application of catalysis-accelerated movement to select for catalytic moieties, or to increase the concentration of catalytic moieties in a sample containing catalytic moieties.

The kinetics of antibody binding to solid-phase immobilized antigen have been investigated (10). However, non-catalytic moieties have not been separated from catalytic moieties on the basis of surface binding. For instance, recombinant phages or recombinant phage infected cells have not been screened or concentrated on the basis of those which express a non-catalytic antibody binding to the substrate with the same affinity, regardless of incubation time, whereas those which express a catalytic antibody or catalytic portion thereof initially binding to the substrate, but dissociating once catalysis has occurred. Nor has surface binding been employed to select for catalytic moieties in a sample containing catalytic moieties.

In addition, while effects of temperature on binding and catalysis by enzymes has been investigated (12), heretofore there has been no use of the discontinuity in the substrate binding of a catalytic moiety (but not of a non-catalyst) as a function of temperature to select for catalytic moieties, increase the concentration of catalytic moieties in a sample containing catalytic moieties or to screen or concentrate recombinant phages or recombinant phage infected cells expressing catalytic moieties.

While principles of "weak affinity chromatography" in the presence of a variety of competing soluble ligands to alter the retention of molecules on chromatographic columns, for instance of a ligand which possesses relatively weak affinity for a moiety covalently coupled to a solid support (17) and catalytic mechanisms (15) have been examined, heretofore there has been no application of changes in binding of catalysts by competition to isolate or select catalysts from non-catalysts or to increase the concentration of catalysts.

It is desired to be able to select for catalytic moieties on the basis of those kinetic and thermodynamic properties intrinsically and essentially associated with catalysis, i.e., reaction-based selection is desired. It is also desired to be able to increase the concentration of catalytic moieties in a sample, and to obtain this increased concentration by exploiting catalytic properties, i.e., obtaining an increased concentration of catalytic moieties on a reaction basis. It is further desired to screen or concentrate a recombinant virus or recombinant virus infected cell population which expresses a catalytic moiety on the basis of catalytic properties, i.e., reaction based selection or concentrating of such a population.

As mentioned earlier, it is also desired to be able to screen a recombinant phage population not only for those members expressing an antibody (e.g., by affinity or hapten binding), but, to also screen this population for members which express a catalytic antibody or portion thereof, a catalytic enzyme, or more generally a catalytic moiety. For instance, selection based on catalytic properties is desired so that those members of the population which so express the catalytic antibody or portion thereof can be used to produce further populations (without substantial contamination by members that do not express the antibody or portion thereof or that express it but not catalytically), or to catalyze desired reactions (with optimal turnover rate due to minimal contamination by or reduced concentration of members that do not express the catalytic antibody or portion thereof). Indeed, in the scenario of attempting to use recombinant phages or the products of recombinant phage infected cells to catalyze a reaction, those members of the population that express the antibody or portion thereof, but not in a catalytically active form, are deleterious to the reaction system because they can compete with catalytic phages or moieties for substrate. Likewise, with respect to using a recombinant phage population to infect cells and produce monoclonal antibodies, reaction based selection of the population is desired to reduce the labor involved in otherwise reducing the population to a smaller population to further create monoclonal antibodies. Thus, it is desired to be able to perform reaction based selection or concentrating of a recombinant phage or recombinant phage infected cell population for catalytic activity.

SUMMARY OF THE INVENTION

The present invention therefore provide same method for selecting catalytic moieties comprising reaction-based selection for moieties with catalytic activity and isolating such moieties. The present invention likewise provides a method for increasing the concentration of catalytic moieties in a sample comprising reaction-based selection for moieties with catalytic activity and isolating such moieties. The selection can be by methods employing a mechanism-based inhibitor, catalysis-accelerated movement, surface binding, discontinuity of binding as a function of temperature, or changes in binding by competition.

The invention further provides a method for selecting a recombinant virus or a cell, e.g., a cell infected by recombinant virus, which expresses a catalytic moiety such as a catalytic antibody or catalytic portion thereof, or for increasing the concentration of such viruses or cells in a sample of viruses or cells comprising:

reaction-based selection for catalytic activity of a population of recombinant viruses or cells suspected of including viruses or cells expressing the catalytic moiety, and isolating from the population a subpopulation which can act catalytically.

Similarly, the invention provides a method for producing a recombinant virus or a cell-line capable of expressing a catalytic moiety such as a catalytic antibody or catalytic portion thereof comprising:

reaction-based selection for catalytic activity of a population of recombinant viruses suspected of including viruses expressing the catalytic moiety, isolating from the population a subpopulation which can act catalytically, and infecting a host susceptible to infection by the recombinant virus with virus of the subpopulation.

The reaction-based selection can be performed by employing a mechanism-based inhibitor, catalysis-accelerated movement, surface binding, discontinuity of binding as a function of temperature, or changes in binding by competition. These embodiments also contemplate repetition. If desired, for instance, the reaction-based selection can be repeated after the isolating step; and, this repetition can be by the same technique (such as repeated catalysis-accelerated movement), or, by a different technique (e.g., catalysis-accelerated movement during a first pass through the reaction-based selection with surface binding, mechanism-based inhibitor, discontinuity of binding as a function of temperature or changes in binding by competition employed during a subsequent, repeated pass through the reaction based selection step).

The invention further provides a method for detecting a recombinant virus or a cell which expresses a catalytic moiety (e.g., a catalytic antibody or catalytic portion thereof), or for increasing the concentration of such viruses or cells in a sample which comprises:

selecting a population of recombinant viruses or cells suspected of including viruses expressing the catalytic moiety for binding to a selected hapten, isolating from the population a first subpopulation which can bind to the selected hapten, reaction-based selection of the first subpopulation for catalytic activity, and isolating from the first subpopulation a second subpopulation which can act catalytically.

Likewise, the invention provides a method for producing a recombinant virus or a cell-line capable of expressing a catalytic moiety comprising:

selecting a population of recombinant viruses suspected of including viruses expressing the catalytic moiety for binding to a selected hapten, isolating from the population a first subpopulation which can bind to the selected hapten, reaction-based selection of the first subpopulation for catalytic activity, isolating from the first subpopulation a second subpopulation which can act catalytically, and, infecting a host susceptible to infection by the recombinant virus with virus of the second subpopulation.

The selection for binding to a selected hapten can comprise passing the population over an affinity column of immobilized hapten. In this regard the isolating of the first subpopulation can comprise eluting that portion of the population which bind to the affinity column.

The selection for catalytic activity can be by employing a mechanism-based inhibitor; for instance, the selection can comprise contacting the first subpopulation with a mechanism-based inhibitor so as to form a reaction mixture. And, the isolating of the second subpopulation can comprise passing the reaction mixture over the hapten affinity column and collecting viruses or cells which do not bind to the immobilized hapten. Contacting of the first subpopulation with the mechanism-based inhibitor can also be performed by contacting the first subpopulation with inhibitor bound to particles, for instance, by passing the first subpopulation over a column to which the inhibitor is bound by a cleavable group; and, isolating the second subpopulation can comprise cleaving the inhibitor-virus (or cell) complexes from the column, or separating the inhibitor-virus (or cell) particle complexes.

Alternatively, the selection for catalytic activity can be by employing catalysis-accelerated movement; for instance, selection can comprise contacting the first subpopulation with a surface including a desired substrate of a catalytic reaction, wherein the contacting is at a first point on the surface, and, after sufficient time for members of the first subpopulation having catalytic activity to move a distance to a second point on the surface, detecting members of the first subpopulation at the second point. In this alternative, isolating the second population can comprise collecting the members of the first subpopulation from the second point on the surface.

In a further alternative embodiment, the selection for catalytic activity can be by surface binding; for instance, selection can comprise contacting the first subpopulation with a surface including a desired substrate of a catalytic reaction to which members of the first subpopulation not having catalytic activity will bind and members of the first subpopulation having catalytic activity will bind and engage in catalysis, and after sufficient time from the contacting for the members of the first subpopulation not having catalytic activity to approach equilibrium with the surface but less than the time from contacting for members of the first subpopulation having catalytic activity to consume said substrate, washing the surface to remove therefrom members of the first subpopulation having catalytic activity; and, isolating the second subpopulation can then comprise collecting the wash. In this alternative embodiment the selection for catalytic activity can further comprise, after contacting the first population with the surface, prior to washing the surface to remove therefrom members of the first subpopulation having catalytic activity and after sufficient time from the contacting for both members of the first population not having catalytic activity and members of the first subpopulation having catalytic activity to bind to the substrate but less than the time from contacting for members of said first subpopulation having catalytic activity to consume substrate or complete catalysis, washing the surface so as to remove any members of said first subpopulation having low or no affinity to the substrate.

In yet a further alternative embodiment the reaction-based selection can be by changes in the enthalpic component of binding as a function of temperature. For instance, the selection can comprise contacting the first subpopulation with substrate at a first temperature, contacting the first subpopulation with the substrate at a second temperature, said second temperature being higher than the first temperature, and thereafter the isolating of the second subpopulation comprises collecting those members of the first subpopulation upon which exhibit the effect of temperature on apparent binding is different. In this embodiment the substrate can be immobilized, for instance on a column, members of the first subpopulation which bind loosely or elute first and those which bind tightly or elute later at the first temperature are collected in fractions; the fractions are again contacted with the substrate at the second temperature and fractions again collected. The fractions collected after the contacting at the second temperature are then analyzed for relative concentration of members of the first subpopulation: the fraction(s) having the lowest concentration(s) contain the members of the first subpopulation with the greatest catalytic activity because the effect of the temperature on apparent binding is different. It is preferred that the first temperature be so low that binding will occur, but not catalysis.

And in even yet another alternative embodiment the selection for catalytic activity can be by changes in binding by competition. For instance, the selection can comprise contacting the first subpopulation with an immobilized non-reactive substrate analog, said contacting being in the presence of mobile non-reactive substrate analog and collecting therefrom a sample or samples which bind to the immobilized analog; contacting the sample or samples with the immobilized analog in the presence of substrate, and collecting therefrom those members of the first subpopulation which exhibit different apparent binding than a majority of the members. For example, if the immobilized analog is non-reactive substrate analog immobilized on an affinity chromatography column, when the sample or samples are contacted with the immobilized column in the presence of substrate, those members of the first subpopulation which exhibit different apparent binding than a majority of the members are fraction(s) which elute later or sooner than the main peak(s).

Again it is mentioned that the methods of the invention encompass repetition of any one step prior to advancing to the next step. For instance, an initial population can be subjected to the selection for binding to a selected hapten, and those that bind can be isolated and the isolated portion again subjected to selection for binding to the hapten, and then those that bind in this second pass through the step are isolated and used in the reaction-based selection step. Likewise, an initial "first subpopulation" can be subjected to the reaction-based selection for catalytic activity, a second subpopulation which can act catalytically is isolated therefrom, this second subpopulation can again be subjected to the reaction-based selection, and, from subjecting the second subpopulation to a second pass through the reaction-based selection step, a second "second subpopulation" can be isolated. Repetition of steps can be used to further enrich and increase the catalytic activity (expression) of the product of the process. The second pass through reaction-based selection can be by the same procedure as the first pass through, or can be by any of the other embodiments of the invention. In addition, the invention provides for further alternatives of the above-described embodiments.

Thus, the present invention also provides a recombinant virus or a cell population capable of expressing a catalytic moiety such as a catalytic antibody or catalytic portion thereof which is produced by the foregoing inventive methods. Such a population is substantially pure insofar as the foregoing methods eliminate most, if not all, viruses, cells or moieties which do not act catalytically, or those which do not bind to the hapten as well as those which do not act catalytically. In addition, the present invention provides a catalyst composition prepared by the foregoing inventive methods. Such a catalyst composition includes the aforementioned virus or cell population, as well as other catalytic moieties; and, such a composition is likewise substantially pure because the foregoing inventive methods eliminate most, if not all non-catalytic moieties, or those which do not bind to hapten as well as those which are non-catalytic. The viruses in the invention can be phages such as M13 phage or fd phage and thus, the host can be bacteria such as *E. coli*.

BRIEF DESCRIPTION OF DRAWINGS

In the following Detailed Description, reference will be made to the accompanying drawings which are hereby incorporated herein by reference and which assist in illustrating the invention without necessarily limiting the invention, wherein.

DETAILED DESCRIPTION

Figure 1:
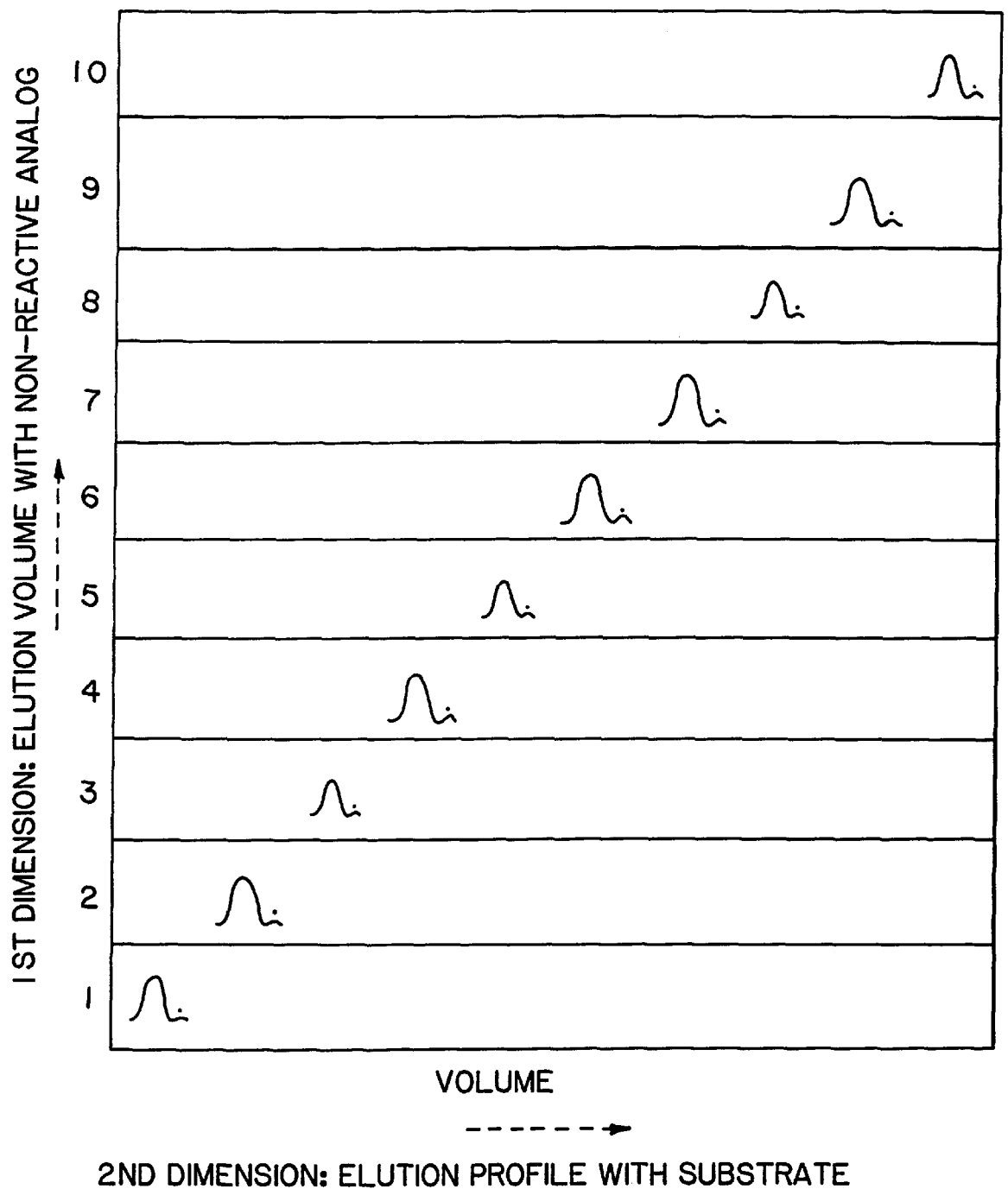
FIGS. 1 and 2 are two dimensional separation profiles with first a dimension elution profile (vol.) with non-reactive analog portrayed vertically and second dimension elution (vol.) profile with substrate portrayed horizontally, and the small starred peaks marking elution after or before main peaks so as to indicate fractions containing catalysts which can then be enriched.

It is assumed that the skilled artisan already appreciates techniques for amplifying and inserting coding for antibody (or portion thereof) expression into the viral genome (1, 2, 3, 4, 11) and thus obtaining a viral population suspected of including members capable of expressing a catalytic moiety; and, it is assumed that the skilled artisan appreciates that such recombinant viruses can be used to infect a host cell such as *E. coli* and that the recombinant virus can exist as a provirus or prophage in the host chromosome with the cell and its progeny expressing the catalytic moiety until a lytic cycle is initiated. It is also assumed that the skilled artisan already appreciates techniques for obtaining a sample containing catalytic moieties. Thus, the following description starts from a population of recombinant viruses or a population of cells suspected of including viruses or cells capable of expressing a catalytic moiety, a catalytic antibody or catalytic portion thereof; or, from a sample, the presence of catalytic moieties therein is to be determined, selected or concentrated.

"Catalytic antibody" and "catalytic portion thereof" (of a catalytic antibody) as used herein is a substance which is capable of changing the rate of a chemical reaction, all other conditions (e.g., temperature, reactant/substrate concentration, etc.) being the same and which is not irreversibly altered by the chemical reaction and, therefore, is not consumed in the reaction. It is also a substance which exhibits the capability of converting multiple moles of reactant/substrate per mole of catalytic antibody; and which, from a mechanistic viewpoint, binds the reactant/substrate, effects the accelerated conversion of the reactant/substrate to the product and then releases the product; and which changes the rate of the chemical reaction without shifting the position of the equilibrium. While the aforementioned definitions are characteristics of ideal catalysts, in practice, even the best of catalysts become inhibited or deactivated by contamination in the reaction system or as a result of chemical or physical destruction during the reaction process. For reasons well-known in the art, the true operation of a catalyst may be obscured by components of the reaction system or by the condition of the reaction environment.

In addition, the term "catalytic moiety" is used herein for any moiety that acts catalytically, and, this expression without limitation includes: a "catalytic antibody"; a "catalytic portion thereof" (of a catalytic antibody); a catalytic peptide, oligopeptide, polypeptide or enzyme or catalytic portion thereof; catalytic molecules expressed by self-replicating systems; entities that contain catalytic molecules or the expression thereof in their genetic coding and may be self-replicating or may not necessarily be self-replicating such as bare mRNA, ribosomes or polysomes to which a catalytic molecule is attached, for instance by the building action of a protein thereon; or the like.

The term "surface-bound" is used herein for any moiety which is bound, for instance, either by physical attractive forces or chemical bonding, to a surface. As used herein, catalytic moieties are preferably surface-bound either directly to DNA or RNA that codes for the catalytic moiety or to an envelope enclosing the DNA or RNA that codes for the catalytic moiety. Such an envelope can include, but is not limited to, cell membranes, viral coats, or cell walls.

The art has adopted certain working definitions to express catalytic activity. These expressions include: (1) $k_{cat}$, or "turnover number"; (2) $k_{cat}/k_{uncat}$, the "rate enhancement factor" and (3) $K_m$, the "Michaelis constant". Turnover indicates the number of molecules of reactant/substrate which can be converted to product per mole of catalytic antibody per unit time. For example, if a molecule exhibits a turnover of $10^3$ of substrate per minute and the molecule maintains its catalytic activity for 24 hours at room temperature and at its optimal pH, each molecule of catalyst would then make a total of $1.4 \times 10^6$ conversions, indicating its catalytic behavior. This total conversion is to be distinguished from the total conversion in a stoichiometric reaction, which will never exceed 1.0, no matter how long the reaction is carried out. The rate enhancement factor is a dimensionless number which expresses the rate of reaction in the presence of catalyst to the rate of reaction in the absence of catalyst, all other reaction conditions being equal. The Michaelis constant is an apparent binding constant. It is equal to the concentration of substrate at which the reaction velocity is one-half maximal ($[S]=K_m$ at $k_{cat}/2$).

In accordance with the invention, an antibody can comprise purified immunoglobulins (IgG, IgM, IgA, IgD or IgE) or antibody fragments, such as, for example, Fab, F(ab')$_2$, Fv, etc., of immunoglobulins. Catalytic antibodies include certain major categories. A first category includes catalytic antibodies which have been rationally designed, i.e., antibodies elicited with an antigen introduced by specific immunization against a target antigen or substrate. Such catalytic antibodies, processes for their preparation and their use are described in U.S. Pat. No. 4,888,281, issued Dec. 19, 1989, U.S. Pat. No. 4,792,446, issued Dec. 20, 1988 and U.S. applications Ser. Nos. 064,239, filed Jun. 19, 1987, and 805,576, filed Dec. 10, 1991; the disclosures of all of which are incorporated herein by reference. A second category of catalytic antibodies includes naturally occurring antibodies which are produced by an animal's immune system to the animal's own cellular component (self-antigen), as opposed to the first category of catalytic antibodies previously described. These "autoantibodies" are described in U.S. application Ser. No. 343,081, filed Apr. 25, 1989, the disclosure of which is incorporated herein by reference. The DNA coding for both of these types of catalytic antibodies or for catalytic fragments thereof can be amplified and be inserted into the viral genome (see 1, 2, 3, 4). A third category includes catalytic antibodies which are generated by methods not involving immunization. For instance, catalytic antibodies can be produced by the randomization of variable regions of previously elicited antibodies to generate antibodies with new specificities, but which were not elicited from immunization.

The term "chemical reaction" refers to a reaction wherein at least one reactant is converted to at least one product. Such chemical reactions include chemical reactions which can be catalyzed by enzymes such as, for example, oxidoreductases, transferases, hydrolases, lyases, isomerases and ligases, as well as chemical reactions for which no enzymes are known such as, for example, oxidations, reductions, additions, condensations, eliminations, substitutions, cleavages and rearrangements. The chemical reaction can also be the cleavage of a peptide bond. Peptide bond as used herein refers to an amide bond linking two adjacent amino acid residues and is generically represented by the following formula wherein the peptide bond is shown within the box:

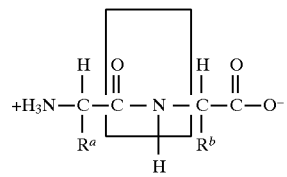

An amino acid consists of a carbon atom to which is bonded an amino group, a carboxyl group, a hydrogen atom and a distinctive group referred to as a "side chain" ($R^a$ and $R^b$ in the formula above). Amino acid as used herein includes but is not limited to the twenty naturally occurring amino acids which comprise the building blocks of proteins. It is understood by those skilled in the art that when either of the adjacent amino acids is proline, the respective side chains $R^a$ or $R^b$ are bonded to the adjacent nitrogen atoms to form the characteristic 5-membered proline ring.

The term "substrate" is synonymous with the reactant in the chemical reaction and can be any of a number of molecules and biomolecules including but not limited to esters, peptides, proteins, phospholipids, carbohydrates (e.g., glycogen, glucose, etc.) and drugs (including abused substances and drugs and prodrugs from exogenous sources). In this regard reference is made to copending applications Ser. Nos. 07/740,501, filed Aug. 5, 1991 and 07/773,042, filed Oct. 10, 1991, incorporated herein by reference. For instance, the substrate can contain an ester bond or bonds, peptide bond or bonds. The substrate can also be any proteinaceous molecule, such as, for example, a regulatory protein or a structural protein including but not limited to peptide hormones (e.g., insulin, growth hormone, secretin, etc.), peptide neurotransmitters, neuromodulators and neurohumoral factors (e.g., VIP, endorphins, enkephlins, bradykinins, substance P, etc.), tumor proteins (e.g., oncogene products, carcinoembryonic antigens, etc.), bacterial proteins and viral proteins including without limitation core and coat proteins (e.g., human immunodeficiency viral (HIV) gp 120 influenza glycoproteins, etc.). The substrate can also be an antigen or a self-antigen, i.e., any antigen which the animal body makes using its own genetic code. Thus, self-antigens are distinguished from foreign antigens (e.g., bacterial, viral antigens). The term "animal" as used herein refers to any organism with an immune system and includes mammalian and non-mammalian animals.

I. Mechanism-based inhibition selection

A. An Overview of the Method

In a general overview of this embodiment of the invention, a virus or cell population potentially bearing a catalytic antibody or catalytic portion thereof, or a sample containing catalytic moieties is preferably:

1. Passed over an affinity column of immobilized hapten. Those that bind are eluted, by for example a change in pH or by passing free hapten over the column. This binding selection is optional.

2. a. Viruses, cells or catalytic moieties found to bind to the hapten affinity column are contacted with, for instance, mixed and allowed to react with a suitably designed mechanism-based inhibitor to form a mixture.

2. b. Alternatively, the mechanism-based inhibitor can be bound to particles such as a column, preferably by a cleavable group. The viruses, cells or catalytic moieties are passed over the column, with those that bind being eluted for further use (e.g., infection) by cleaving the inhibitor from the column, or, by passing a suitable solution, for instance an acidic solution, over the column, to dissolve the virus' or cell's coat and eluting the DNA therefrom, and thereafter using the DNA to transfect host cells or produce recombinant cells or viruses.

3. In the scenario of alternative 2.a. of this embodiment, after an appropriate length of time, the mixture of viruses, cells or catalytic moieties is chromatographed or re-chromatographed on the hapten affinity column. This time the viruses, cells or catalytic moieties that flow through (that do not bind to hapten) are collected. These viruses or cells are used to infect a suitable host such as *E. coli* or are induced to undergo a lytic cycle and the viruses resulting therefrom, e.g., from host infection or lysis are scaled up for catalytic use or further selection for catalysis.

This embodiment, in more detail, is as follows:

B. Hapten Affinity Chromatography

In preferred embodiments, before catalytic selection by mechanism-based inactivation, the antibody expressing viruses or cells or the catalytic moieties are pre-selected, for instance, by hapten affinity chromatography. However, catalytic selection can be performed without first pre-selecting by hapten binding. In a preferred embodiment, those viruses, phages, cells or moieties (>6000) that bind hapten are submitted to reaction with a mechanism-based inhibitor. Affinity chromatography of viruses bearing antibodies using immobilized hapten has been successfully carried out in the literature (2, 3, 4). In the current invention, the first step in the selection of catalysts is preferably to use binding such as hapten affinity chromatography. For example, if hydrolysis of the following ester substrate (II) is desired the following hapten (I) can preferably be used:

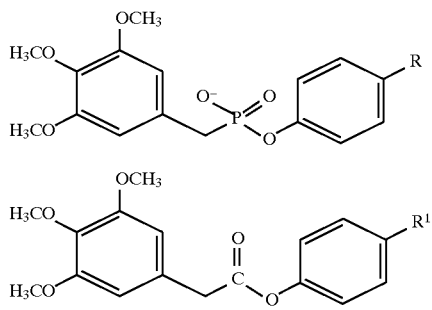

For the hapten (I), R is a linker to a conjugate protein during immunization (e.g., KLH or BSA) and to a solid matrix such as a column during affinity chromatography and for the substrate (II), $R^1$ is —H or —$NO_2$.

Likewise, for hydrolysis of the following esters (IIA) and (IIB), the following haptens (IA) and (IB) can preferably be used:

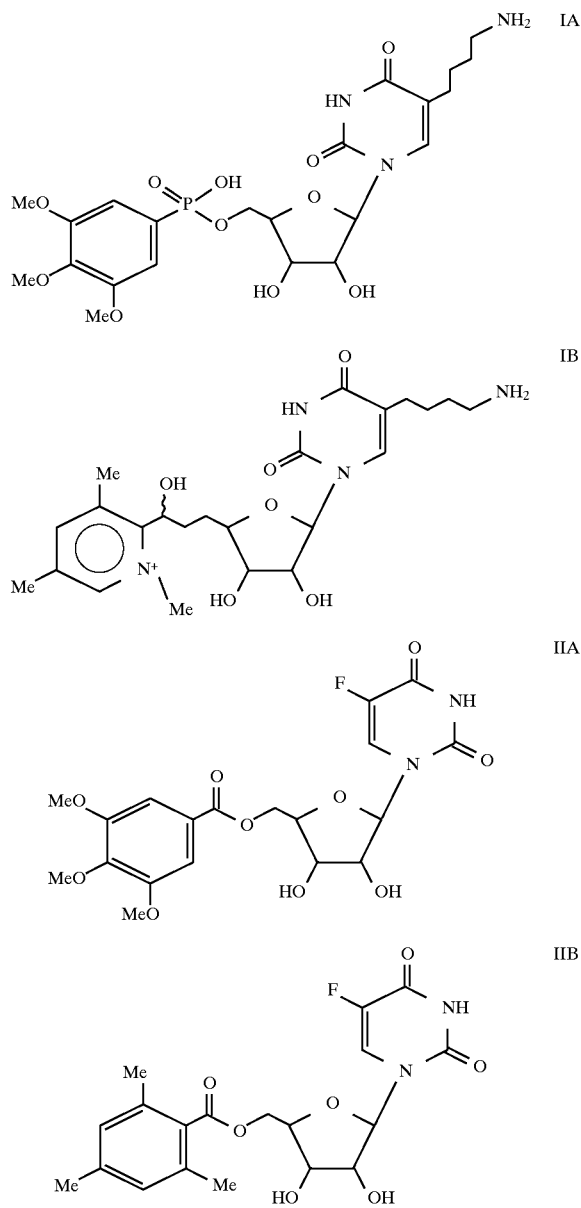

For these structures, Me=methyl group; and, reference is made to copending application Ser. No. 07/773,042, filed Oct. 10, 1991, incorporated herein by reference, which describes the production and use of these compounds.

Those viruses, cells or moieties that bind to the hapten are eluted by a change in pH or with free hapten (followed by dialysis to remove bound hapten) and are then subjected to the next step; namely, exposure to mechanism-based reactant(s).

C. Reaction With Mechanism-Based Inhibitors

In this step the isolated subpopulation that binds to the hapten is contacted with a suitable mechanism-based inhibitor (affinity label or suicide substrate). A suitable mechanism-based inhibitor forms an irreversible adduct with a catalytically active antibody or portion thereof, for instance, a catalytic moiety expressed on the outer surface of the virus, phage, or cell whereas such an inhibitor does not form an irreversible adduct with a virus or cell which expresses the antibody or portion thereof but not catalytically. Below are described mechanism-based inhibitors of ester-hydrolyzing antibodies that may be expected to arise from immunization with haptens I, IA, or IB. Other mechanism-based inhibitors are well known that inactivate reactions other than ester hydrolysis and could be used to select catalytic moieties, such as catalytic antibodies, capable of catalyzing other reactions. Catalytic reactions for which exist mechanism-based inhibitors include synthetase, peptidase, oxidation/reduction, β-lactamase, decarboxylation, aminotransferase, lyase, racemase, and hydroxylase reactions (5). Design and use of similar inhibitors could be carried out by one skilled in the art for these and other reactions.

For instance, with reference to the above-mentioned esterolytic reactions the following structures are mechanism-based inhibitors:

(i) Hydrolysis of ester substrate (II):

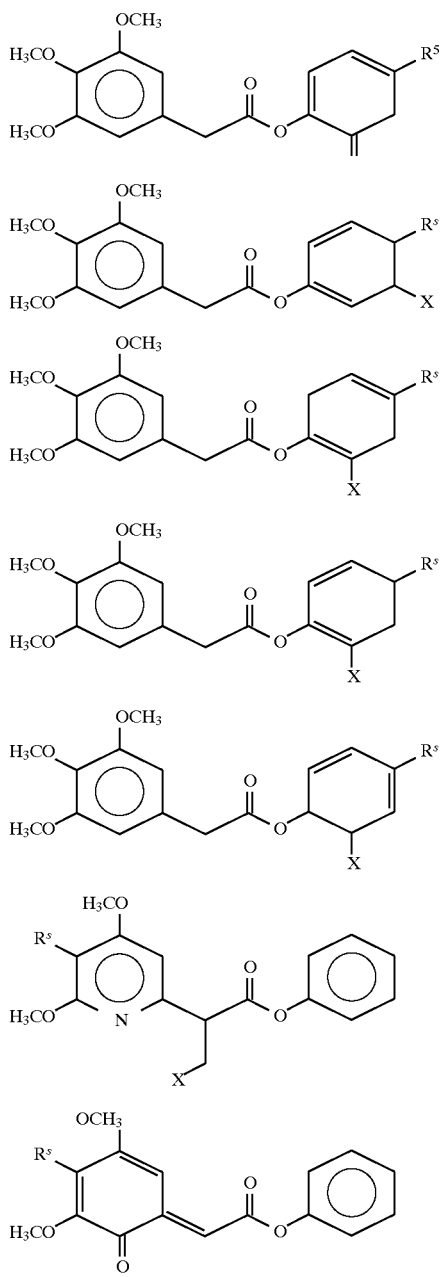

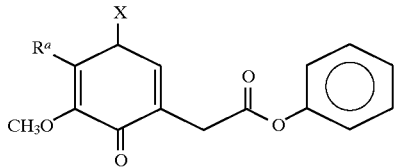

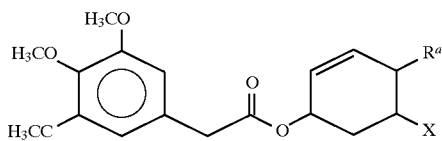

wherein $R^s$ is linkage to particles which may be packed in a column or suspended in a fluid (mobile) and x is a leaving group such as Br, I, $OSO_2CH_3$ or the like. The linkage, of course, need not be present if the inhibitor is used in a mobile form.

Thus, in the instance of a catalytic antibody elicited by hapten (I) (or a phage or cell or the like which produces such a catalytic antibody or a catalytic portion thereof) contacted under reaction conditions with substrate II, the following occurs:

That is, a complex forms between the substrate and the catalytic moiety, e.g., catalytic antibody, which results in products (i) and (ii) and the regeneration of the catalyst.

However, in the instance of inhibitors (III) to (XI), while a reaction of the inhibitor occurs when contacted under reaction conditions with the catalytic antibody elicited by hapten (I), a portion thereof remains bound to the catalyst, thereby preventing it from engaging in further catalysis (preventing regeneration) and thus allowing for its isolation according to the invention, as shown in the following Table I.

TABLE I

| Inhibitor | Reactive Product | Binding Site Specificity |
|---|---|---|
| III | | Michael Acceptor for, thiol alcohol, phenol residues can form enamine w/amino |
| IV | | Michael Acceptor for, thiol alcohol, phenol residues can form enamine w/amino |
| V | | Alkylating agent for thiol, alcohol, phenol, amino, and carboxyl residues |
| VI | | Alkylating agent for thiol, alcohol, phenol, amino, and carboxyl residues |
| VII | | Alkylating agent for thiol, alcohol, phenol, amino, and carboxyl residues |

TABLE I-continued

| Inhibitor | Reactive Product | Binding Site Specificity |
|---|---|---|
| VIII | | Michael Acceptor for, thiol alcohol, phenol residues |
| IX | | Michael Acceptor for, thiol alcohol, phenol residues can form enamine w/amino |
| X | | Michael Acceptor for, thio alcohol, phenol residues can form enamine w/amino |
| XI | | Michael Acceptor for, thiol alcohol, phenol residues can form enamine w/amino |

(ii) Hydrolysis of ester substrate (IIA):

Likewise, for the 5-fluorouridine esterase reaction, i.e., the hydrolysis of compound (IIA) or (IIB) to yield 5-fluorouridine by contacting the compound (IIA) or (IIB) with an appropriate catalyst under reaction conditions (e.g., a catalytic antibody elicited by hapten (IA) or (IB), or a phage or cell or the like so expressing that catalytic antibody or a catalytic portion thereof), the following Table II provides inhibitors of the catalyst; and the portion of the inhibitor ("reactive product") which remains bound to the catalyst; x and $R^s$ are as defined above.

TABLE II

| Inhibitor Product | | Reactive Product |
|---|---|---|
| XII | (structure) →Catalyst→ | (structure) |
| XIII | (structure) →Catalyst→ | (structure) |
| XIV | (structure) →Catalyst→ | (structure) |

TABLE II-continued

| Inhibitor Product | | Reactive Product |
|---|---|---|
| XV | | |
| XVI | | |
| XVII | | |
| XVIII | | |

TABLE II-continued
| Inhibitor | Product | | Reactive Product |
|---|---|---|---|
| XIX | 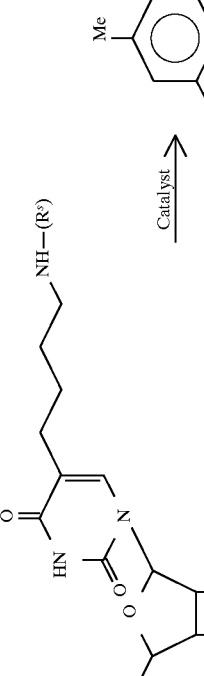 | Catalyst → | 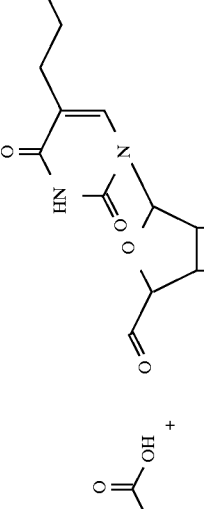 |
| XX | 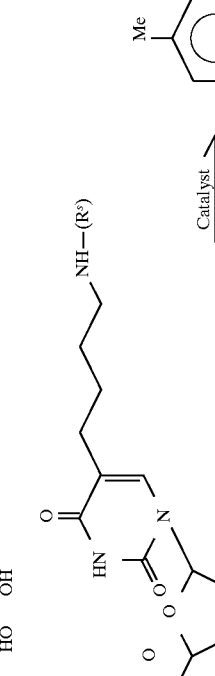 | Catalyst → | 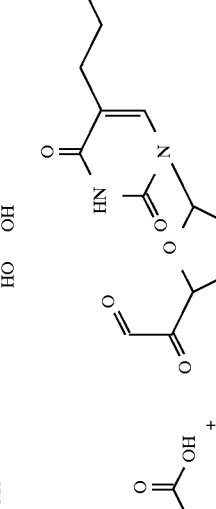 |

In the above esterolytic reactions the conditions are generally: pH 6.0 to 8.0, typically 7.0, 10 to 100, such as 30 to 70, typically 50 mM Hepes, 100 to 300, such as 100 to 200, typically 150 mM NaCl, temperature of 20° to 40° C. usually 30° C, and time of 0.5 to 3 hours.

D. Separation of Viruses or Moieties by Affinity Sorting

Following incubation, the viruses or cells bearing the antibody or portion thereof and that are catalytic, i.e., that have reacted with the mechanism-based inhibitor, no longer bind hapten; but, those phages or cells bearing antibodies that did not react with the reactant will continue to bind to hapten. Thus, a separation of viruses or cells displaying the catalytic antibody or the catalytic portion thereof from non-catalytic viruses or cells can be carried out definitely by a second round of hapten affinity chromatography. This is carried out as described above, and does not require separation of the viruses or cells from unreacted mechanism-based inhibitor. Catalytic antibody phages or cells do not bind to the column but non-catalytic phages do so bind. Thus, viruses or cells that pass through the column unbound are the phages which express the catalytic antibody or portion thereof. These viruses are used to infect a suitable host; for instance, if the viruses are phages such as M13, fd or lambda, $E.$ $coli$ is a suitable host. After infection, the antibodies encoded in the viral DNA vector are scaled up for further use or characterization. In particular, by so infecting $E.$ $coli$ with these phages, the $E.$ $coli$ can become a factory for the production of phages which express the catalytic antibody or portion thereof; or, for the expression of the catalytic antibody or catalytic portion thereof. The viral product or expression of the infected $E.$ $coli$ is then used catalytically, e.g., in ester hydrolysis, or, in further selection as herein described to produce virus (phage) and host (e.g., $E.$ $coli$) lines which are catalytically most active. Likewise, if cells have been so catalytically screened and those that elute are collected, the cells can then be used to express the catalytic product; or, if the cells so express the catalytic product due to viral infection (with the virus being a provirus or prophage), the cells can also be induced to undergo a lytic cycle.

Alternatively, the inhibitor is bound to particles. In a broad sense, a column is an example of particles, but they are "packed" (immobilized). The inhibitor is preferably bound to the particles through a cleavable group such that the reaction with the inhibitor is performed by contacting the viruses, cells or catalytic moieties with the particles, e.g., passing them over the column. In the use of a column, non-catalysts elute, while catalysts bind; and, the catalysts are separated by cleaving the inhibitor-catalyst complex from the column, or by otherwise causing disassociation from the inhibitor; for instance, in the case of viruses, phages or cells, by passing a suitable liquid over the column, e.g., an acid, and eluting the DNA therefrom for further use (transfection, recombination).

In particular, catalytic phages, viruses, cells or moieties selected with a specifically-designed mechanism-based inhibitor can be separated from non-catalysts using affinity chromatography if the inhibitor is immobilized to a solid matrix such as a column. In this embodiment it is desired to be able to recover catalysts after they have reacted with the immobilized inhibitor. To achieve this, the inhibitor can be attached to the column via a molecule or molecules (a "cleavable group" or linkage) that can be readily cleaved or dissociated from the column matrix, to allow recovery of catalysts. The cleavable group can link the inhibitor to the column matrix either noncovalently or covalently.

In practice, a suspension of phages, viruses, cells or moieties, in a suitable buffer is eluted over a column on which an appropriate inhibitor has been immobilized via a cleavable group. The experimental procedure is depicted in the scheme below wherein on the left is an example of a covalent cleavable group and on the right an example of a noncovalent dissociable linkage. Catalysts are able to react with the inhibitor and covalently attach to the column (support) via the inhibitor (center figure on both left and right) while those entities not able to react with the inhibitor wash through the column (not shown in scheme). The column is then washed with approximately 5 column volumes of the initial elution buffer.

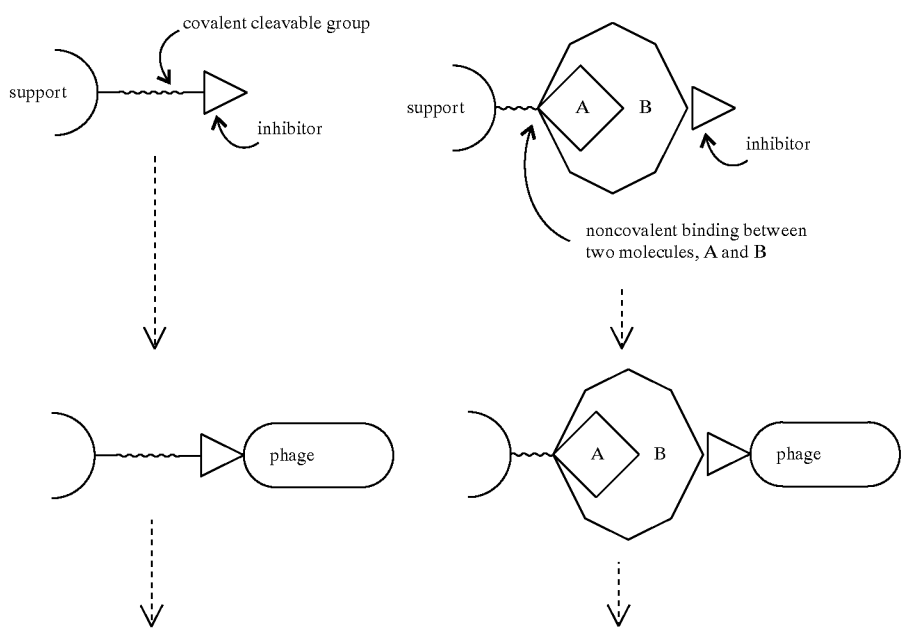

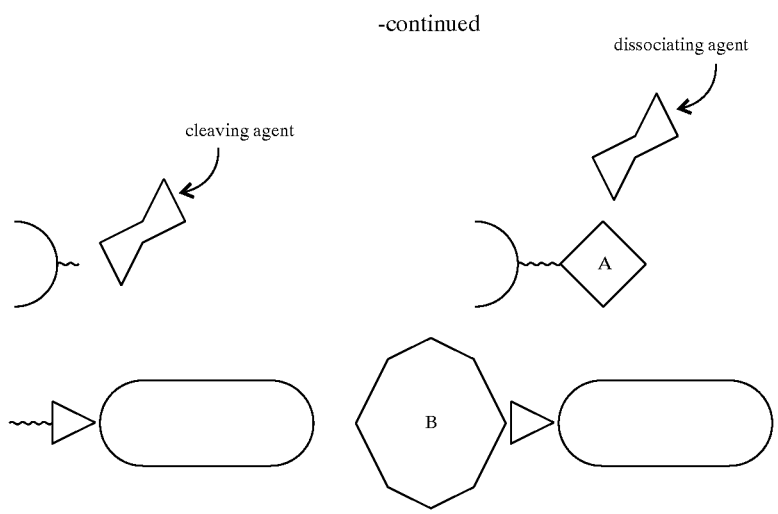

The buffer is chosen to optimize the reaction between the catalyst and the inhibitor. Following the buffer wash, elution conditions are changed to cause cleavage (lower left in scheme) or dissociation (lower right in scheme) of the cleavable group to allow recovery of entities (catalysts) that have reacted with the inhibitor.

Noncovalent interactions provide a useful way of attaching an inhibitor to a solid matrix. The inhibitor is covalently attached to a ligand which is able to interact with the column in a dissociable noncovalent manner. The column is a standard solid matrix such as Sepharose 6B altered to display moieties that specifically and tightly interact with the ligand attached to the inhibitor. (A general example would be the immobilization on a column of an enzyme inhibitor. The inhibitor can reversibly and noncovalently bind to its corresponding enzyme whose surface has been covalently modified to display one or more molecules of suicide substrate.) The interaction between modified column and ligand is of high affinity until the experimenter intentionally disrupts it by changing the contents of the eluting solvent system (21, 22). The nature of the changes made in solvent system to elute the ligand are dependent on the choice of the noncovalently interacting pair of molecules, and can be determined by the skilled artisan without undue experimentation. Examples of changes in elution conditions include: ligand competition, allosteric modification, substrate elution, inhibitor elution, ionic strength changes, solvent changes to organic solvents or aqueous/organic mixtures, temperature changes, buffer or pH changes, metal elution, metal chelate elution, chaotropic reagents, or electrophoretic desorption (23). Specific examples of interactions that can be used to noncovalently (but tightly) bind an inhibitor to a solid support are listed below in Table III. See also Pierce, Amicon, Sigma Chem. Co. catalog incorporated herein by reference 24; 25, 26; 27):

TABLE III*

| Attached to solid support: | Attached to suicide substrate: |
|---|---|
| antigen (e.g., dinitrophenyl group) | antibody |
| antibody | antigen |
| cofactor | enzyme |
| enzyme | cofactor |
| protein A,G | antibody |

TABLE III*-continued

| Attached to solid support: | Attached to suicide substrate: |
|---|---|
| carbohydrates, glycoproteins | lectins |
| lectins | carbohydrate, glycoproteins |
| heparin | blood proteins |
| blue A dye | various proteins including: calmodulin serum albumin hormone receptors renin |
| red A dye | various proteins including: alkaline phosphatase carboxypeptidase G peptide hormones |
| matrix gel PBA (boronate ligand) | RNA plasma proteins tRNA serine proteases |
| iminobiotin | avidin |
| avidin | iminobiotin |
| immobilized metal | $\alpha_2$-macroglobulin carboxypeptidase A |

*(see catalogs of Pierce, Amicon, Sigma Chem Co. for immobilized matrices or instructions on immobilization)

Inhibitors can be linked to molecules listed in the right-hand column by standard methods such as carbodiimide coupling and others used in immunology to couple haptens to keyhole limpet hemocyanin or bovine serum albumin.

As stated above, the elution conditions necessary to dissociate the noncovalent complex will depend on the molecule pair chosen. Some specific examples of eluents are listed below in Table IV (see also 21).

TABLE IV

| Associated Molecular Pair: | Disruptive Solutes: |
|---|---|
| protein A/antibody | acetic acid or glycine |
| concanavalin A/oligosaccharide | α-D-methylmannoside or borate buffer or α-D-methylglucoside |
| blue A dye/albumin | salt or urea |

TABLE IV-continued

| Associated Molecular Pair: | Disruptive Solutes: |
| --- | --- |
| immobilized zinc/carboxypeptidase A | EDTA or o-orthophenanthroline |
| iminobiotin/avidin | biotin or pH4 |
| matrix gel PBA/trypsin | boronate ion |

An alternative to noncovalent cleavable interactions, the cleavable group can be covalently attached to both the column and the inhibitor. One way in which covalent cleavable groups can be disrupted is to make them enzyme substrates. The group can then be cleaved by passing the appropriate enzyme through the column which will catalytically cleave the group, releasing the inhibitor and attached catalysts. Perhaps the most versatile of examples of enzymatic cleavage is the use of proteinase enzymes. The inhibitor and the column matrix can both be coupled to the protein substrate resulting in a "column--proteinase substrate-- inhibitor" linkage where "--" represents a covalent bond. Exposure of the linkage to an appropriate protease hydrolyzes the proteinase substrate, releasing the inhibitor from the column allowing recovery of attached catalysts. coupling procedures for attaching the proteinase substrate to the column and to the inhibitor are well established using commercially available reagents (See. e.g. Pierce Chemical Co. catalog).

Specific examples of peptide covalently-attached cleavable groups and the enzymes that can be used to cleave them are shown below in Table V. All proteinases and substrates listed are commercially available in a purified form (from Boehringer-Mannheim, for example):

TABLE V

| Proteinase Releasing Agent: | Substrate Cleavable Group: |
| --- | --- |
| ancrod | fibrinogen |
| elastase | elastin |
| | casein |
| ficin | casein |
| pepsin | IgG |
| | hemoglobin |
| subtilisin | casein |
| thermolysin | casein |

Other covalent linkage groups may be cleaved using mild chemical methods. Table VI, below, lists some functionalized matrices, available from commercial sources, which can be linked to inhibitors having a thiol or amino group, and which can be detached by treatment with thiols. Table VI also lists linkage groups between the matrix and substrate required, and references to their use.

TABLE VI

| Matrix | Linkage | Reference |
| --- | --- | --- |
| Activated Thiol-Sepharose 4B | (direct) | (28) |
| Activated Thiopropyl-sepharose 6B | (direct) | (28) |
| Mersalyl-Trisacryl | (direct) | (29) |
| Avidin matrix | NHS-SS-biotin | (30) |
| Avidin matrix | HPDP-biotin | (30) |

Two protocols can be followed. In one protocol, the functionalized suicide substrate is reacted with the activated matrix or matrix/linkage. The suspension of viruses, phages, cells or moieties is then eluted through the column and allowed to react with the inhibitor. After washing out the noncovalently attached viruses, phages, cells or moieties, the immobilized phages, viruses, cells or moieties can be detached from the column by eluting with a thiol such as mercaptoethanol.

In the other protocol, the functionalized inhibitor is reacted with the suspension of viruses, phages, cells or moieties. Phages, viruses, cells or moieties with catalytic activity are covalently bound by the inhibitor. After an appropriate time, the suspension of viruses, phages, cells or moieties is eluted through the column of activated matrix or matrix/linkage. Only those phages, viruses, cells or moieties having catalytic activity are retained via reaction of the thiol or amino group of the inhibitor with the activated matrix or linkage group. These viruses, phages, cells or moieties can then be detached by treatment with a thiol.

It is also noted that procedures akin to the foregoing for attaching an inhibitor to a column can also be employed for attaching an inhibitor to mobile particles, or for attaching non-reactive substrate analog or substrate to a column or membrane, as discussed below with respect to the further embodiments of the invention.

Alternatively, the inhibitor can comprise or be bound to mobile (suspended) particles which are not "packed" or immobilized, i.e., particles which are not in a column. In this instance, the viruses, cells or catalytic moieties are contacted with the particles. Again, catalysts bind to the particles, while non-catalysts do not. Thus, to separate the catalysts from the non-catalysts, after contacting, the particles are separated from the contacting medium, for instance, by gravity, filtration, centrifugation, electrophoresis, or by magnetic field (if the particles are magnetically responsive). After the particles are isolated, it is preferred to wash them so as to remove any non-catalysts which may have been included with the particles during separation.

The particles advantageously comprise micro-particulate matter having a diameter of 0.001 to 200 $\mu$m, such as 0.05 to 200 $\mu$m or 0.001 to 100 $\mu$m, preferably 0.1 $\mu$m to 100 $\mu$m, most preferably 0.5 $\mu$m to 10 $\mu$m, and a surface component capable of binding to the inhibitor. For example, the microparticulate matter may be crosslinked starch, dextrans, cellulose, proteins, organic polymers, styrene copolymer such as styrene/butadiene copolymer, acrylonitrile/ butadiene/styrene copolymer, vinylacetyl acrylate copolymer, or vinyl chloride/acrylate copolymer, inert inorganic particles, chromium dioxide, oxides of iron, silica, silica mixtures, and proteinaceous matter, or mixtures thereof. A wide range of particles can be employed in the particle-based embodiments of the invention. Generally the particles have a density of from 1.0 to 5.0 g/mL and preferably have a density of from 1.1 to 2 g/mL. Choice of the optimum density is within the skill of the art, the rate of settling in gravity-driven separation being a consideration.

Wide ranges of concentration of particles in the inhibitor composition can also be employed. For example, the concentration can range from 1 to 10,000 $\mu$g/mL to preferably from 5 to 1000 $\mu$g/mL.

In the filtration mode of performing the invention, the filtration means desirably has a pore size, measured as mean diameter, from broadly 0.01 to 90% of the mean diameter of the particles and preferably from 10% to 90% of that diameter. The pore size of the filter should be such as to allow non-catalysts to pass therethrough, while preventing particles to which catalysts bind from passing.

The art has described a number of magnetic particles which can be used in the inhibitor compositions of the invention. For example, U.S. Pat. Nos. 4,628,037, 4,695, 393, 4,698,302, 4,554,088, U.K. Patent Application GB 2,005,019A and EP 0,180,384, all incorporated herein by reference, describe a variety of magnetic particles which can be used with success. The particles may be paramagnetic or ferromagnetic and may be coated with various materials to which inhibitor compounds are coupled so that the magnetic particle can be used in the invention. Desirably the magnetic particles used in the invention have a susceptibility of at least 0.001 cgs units and desirably the susceptibility is at least 0.01 cgs units. The magnetic particles may have a broad range of densities, i.e. from substantially less than that of water, 0.01, to 5 g/mL and preferably from 0.5 to 2 g/mL. The particle sizes can range from 0.001 to 200 such as 0.001 to 100 $\mu$m and preferably from 0.01 to 10 $\mu$m. The concentration of the particles may range broadly from 1 to 10,000 $\mu$g per mL and preferably is from 5 to 1000 $\mu$g per mL.

Desirably, the magnetic particles which are used have a low magnetic resonance, as described for example in EP 0,180,384, so that after the magnetic field is removed, the particles demagnetize. Desirably the density, concentration and particle size of the magnetic particles is chosen such that the settling time is at least 0.5 mm/min and desirably it is above that rate. With respect to particles and particle-based separation methods, including electrochemiluminescence particle-based separation methods which can advantageously be used in the practice of this invention, reference is made to copending applications Ser. Nos. 07/539,389, filed Jun. 18, 1990 and 07/652,427, filed Feb. 6, 1991, both of which are incorporated herein by reference.

II. Selection By Catalysis-Accelerated Movement
A. An overview of the Method Before catalytic selection the virus or phage or cell population or sample of catalytic moieties is preferably selected by hapten affinity chromatography. Those viruses, cells or moieties (>6000) that bind to hapten are preferably then submitted to catalytic selection.

This method involves a flat moist membrane or other two-dimensional surface which is covered, either through covalent attachment or not, by the desired substrate of the catalytic reaction. The optimal surface substrate concentration can be determined without undue experimentation by the skilled artisan for a particular substrate and membrane. Using a suitable instrument such as a very sharp instrument, a paste-like mixture of virons or cells potentially expressing the catalytic moiety, e.g., catalytic antibody, or a sample potentially containing a catalytic moiety, is applied to, preferably streaked in a very fine line across, the surface (a first point on the surface). To visualize the streak a small amount of dye, such as bromphenol blue, may be added to the paste. After a suitable length of time (typically 8 hours to three days but can be otherwise depending upon the particular substrate, i.e, depending upon the reaction being catalyzed and the conditions thereof; and can be determined without undue experimentation by the skilled artisan), the surface of the membrane is scraped preferably with a sharp instrument such as razor blade at a second point a suitable distance from the first point, for instance 0.05 to 0.15 mm, typically 0.10 mm from the first point (or line). To aid in the visualization of the small distance, the scraping can be carried out with the assistance of a low power microscope. Viruses or cells bearing catalytic moieties such as catalytic antibodies, or more generally, catalytic moieties, are present in the scrapings, having moved by catalysis-accelerated movement while viruses or cells bearing non-catalytic antibodies or non-catalytic moieties will not have so diffused. This process can be repeated to enrich the population or concentration of catalytic moiety expressing viruses, phages, or cells or more generally, of catalytic moieties, before scaling up for further use in catalysis or for use in producing a next phage generation (e.g., by infecting a host such as *E. coli*). The process can also be enhanced by the use of electrophoresis. That is, the movement or diffusion of catalytic moieties or of viruses or cells bearing catalytic moieties can be enhanced by applying a potential gradient across the surface.

B. The Surface

The surface can consist of a number of various materials, agarose, starch, polyacrylamide, nylon, activated nylon, Immobilon AV (Millipore, Corp.), glass or nitrocellulose, for example. Important features in this embodiment are that the surface should be able to support (covalently or noncovalently) the substrate of choice, the viruses or phages or cells or catalytic moieties should have some weak attraction for the surface, and it should be able to retain moisture without being immersed for the suitable time periods, e.g., 8 hours to 3 days (possibly in an artificially-humid environment). The concentration of substrate on the surface cannot be so small that the individual substrate molecules are separated by large distances (>1000 angstroms). The surface is desirably covered with a confluent monolayer of substrate wherein individual substrate molecules are separated preferably by no more than 500 angstroms, more preferably by no more than 100 angstroms, and most preferably by no more than 50 angstroms. Concentrations of substrate greater than a confluent monolayer are acceptable and in some cases may be preferable to a monolayer. One skilled in the art is able to determine, without undue experimentation, based on weight, ultraviolet absorbance or other quantitation method, the concentration of substrate to be applied to the surface. If some other component in addition to catalysis-accelerated movement is desired to assist in phage separation, such as an affinity chromatography component, the surface should be capable of serving in that capacity. For example, if phage movement is to be accelerated by electrophoresis across the substrate surface, the surface should be capable of having an electric potential applied to it.

C. Application and Incubation of Viruses, Cells or Moieties Expressing The Catalyst The viruses or phages or cells or catalytic moieties are applied to the substrate surface as a moist paste or very concentrated solution preferably using fine needled syringe. To be able to see where viruses, phages, cells or catalytic moieties have been applied, a small amount of a dye such as bromphenol blue can be added to the sample before application. The phages or cells or catalytic moieties are preferably then incubated on the surface in a suitable environment, e.g., a humidity which is in excess of 50% or is "moist"; a suitable temperature such as 20° to 40°, typically 25° or 37° C. for a time period depending on conditions, which is typically between 8 hours and three days.

D. Selection of Viruses, Cells or Moieties Expressing Catalytic Activity

Following incubation, the surface is preferably placed under a low power microscope or vision is otherwise assisted. A razor blade or other sharp instrument is used to scrape the surface along a line on one or the other or both sides from the original point if it is substantially a line, approximately 0.05 to 0.15, typically 0.10 mm from the original point; alternatively, if the original point was not applied substantially as a line, the scraping can be along substantially a circumference or substantially a circle having a radius 0.05 to 0.15, typically 0.10 mm form the original point. Catalysts are more mobile than non-catalysts and hence there is a concentration of catalysts in the scrapings.

This procedure can be repeated for further enrichment or concentration of the catalytic phage or cell population (i.e., to produce a population which is most catalytically active). Likewise, this procedure can, in general, be used to increase the concentration of catalytic moieties in a sample.

It may be necessary in certain situations to remove those viruses, phages, cells or moieties that do not bind to substrate, for instance, those which bind hapten but not substrate, since they may diffuse readily on the substrate surface. This is accomplished by, immediately upon streaking, quickly and lightly washing the surface or blotting the surface with hapten. In this instance the viruses, phages, cells or moieties which bind hapten but not substrate will initially diffuse quicker than those which bind substrate (and are either catalytic or non-catalytic); and thus, these substrate-non-binding hapten-binding and substrate-non-binding viruses, phages, cells or moieties can immediately be-isolated and removed from the substrate surface. Non-catalyst diffusion is not a serious problem.

Likewise, in certain instances it may be desired to enhance diffusion by applying a potential across the membrane surface, i.e., to enhance diffusion by electrophoresis. Typical conditions for electrophoresis-enhanced movement are empirically determined by the skilled artisan, without undue experimentation, taking into account such factors as the medium (non-bound matter on surface, e.g., moisture on surface as substrate has attraction to surface) the material being diffused (phage, cell, catalytic moiety), and the like, so that there is an optimum between the charge on the material and a minimizing of conductivity of medium, and this promotes maximum separation. The distance for scraping (collecting catalysts) from the original point of application to the surface is accordingly adjusted when movement by catalysis is enhanced by electrophoresis.

III. Catalytic selection By Surface Binding
A. overview

This embodiment is a method to select for catalytic activity from among an extremely large number of viruses, cells or moieties some displaying different antibodies or moieties (e.g., catalytic versus non-catalytic). This method can be used for detection of catalytic activity, e.g., to detect expression of a catalytic moiety; or for increasing the catalytic moiety concentration of a sample. It is based on the observation of tight-binding by a non-catalytic moiety such as an antibody which binds substrate and becomes immobilized on a membrane or other two-dimensional surface with the same affinity regardless of incubation time. On the other hand, a catalytic moiety such as a catalytic antibody or catalytic portion thereof initially binds to the substrate, but once catalysis has occurred it no longer binds to the solid surface. That is, after sufficient time for non-catalysts to approach equilibrium with the surface, but less than the time from contacting for catalysts to consume the substrate on the surface, the non-catalysts remain bound to the surface whereas catalysts can be washed therefrom (collected).

This catalytic selection embodiment preferably involves an initial selection for hapten binding moieties, e.g., antibodies, from weakly- or non-hapten-binding moieties, e.g., antibodies. This can preferably be done by the above-described procedures involving affinity chromatography (2, 3, 4) or filter-lift methods (31). Likewise, in other embodiments herein, if an initial selection for hapten binding moieties is performed, filter-lift methods may be used. Following selection of a subset of viruses, phages, cells or moieties by hapten binding, the viruses, phages, cells or moieties are then screened for substrate catalysis, i.e., reaction based or catalytic selection.

Catalytic selection in this embodiment preferably involves immobilization such as covalent immobilization of substrate on a membrane, such as Immobilon AV (Millipore Corp., Bedford, Mass.). To the membrane surface, a solution of viruses, phages, cells or moieties is added. Alternatively, viruses, phages, cells or moieties can be directly transferred by pressing the substrate-membrane against a sample such as infected host, e.g., bacterial colonies, to lift associated virus or phage antibodies. Substantially immediately, the membrane is preferably washed with a suitable buffer to quickly remove viruses, phages, cells, or moieties, e.g., antibodies, with a low or no affinity for the substrate. The washing step can be carried out by surface washing or by flow through of the buffered wash solution (buffered at a selected pH, e.g., 5.0 to 9.0 such as 7.0 and containing greater than 100 mM NaCl). Thereafter, the membrane is preferably washed with buffer again. Non-catalytic phages, viruses, cells or moieties, e.g., antibodies, that bind tightly will not elute from the membrane, but viruses, phages, cells or moieties which are catalytic, e.g., viruses, phages or cells bearing a catalytic antibody or catalytic portion thereof (or such antibody or portion thereof lifted from infected colonies) that have catalyzed enough substrate to become unbound, will elute. The wash can be concentrated and used catalytically or to reinfect a host such as E. coli. Further enrichment of a phage, virus, or cell population bearing a catalytic antibody or catalytic portion thereof can be accomplished by repeating the procedure. Likewise, the procedure can be used to increase the catalytic moiety concentration of a sample.

In the procedure, the viruses, phages, cells (or antibody therefrom) or moiety should remain in the local areas of the membrane with extremely limited diffusion, such that catalytic phages, viruses or cells (or antibody therefrom) or catalytic moieties exhaust their local supply of substrate and do not move a great distance to bind uncatalyzed substrate. Moreover, if diffusion takes place the catalytic phages, viruses or cells (or antibody therefrom) or catalytic moieties then catalyze substrate in competition with binding, non-catalytic phages, viruses or cells (or antibody therefrom) or with non-catalytic moieties such that the non-catalysts will have a depleted substrate supply and will also easily wash off the membrane. To prevent migration of catalytic moieties, e.g., catalytic phage, virus or cell moieties such as antibodies, it is preferred to keep the membrane as free from excess moisture, e.g., water, as possible and to only keep it moist; for instance, in a humidified chamber. Also, the incubation times may best be minimized so as to prevent diffusion. Secondary washes to selectively remove catalysts can take place at suitable times such as intervals between 0.5 to 16 hours, typically at 1 hour, 3 hours, 6 hours, and 12 hours.

B. Immobilized Substrate

The substrate is preferably modified in the same way as the hapten in affinity chromatography so that the substrate has a linker through which it can be coupled to the membrane. This substrate linkage is akin to that used to bind inhibitors to particles in the Mechanism Based Inhibition Selection embodiment of the invention, and vice versa. The details of the chemistry thereof may depend on the particular substrate chosen but can be closely based on the chemistry used in the hapten preparation; for instance, if initial selection for hapten-binding moieties is performed, and is preferably very similar, if not identical thereto.

C. Membrane

Substrate can be coupled via a linker to the membrane, for instance, any of the surface materials described above with respect to selection by catalysis accelerated movement, such as Immobilon-AV membrane. The coupling can be by known procedures for instance according to procedures such as the recommendations of the membrane supplier (Millipore) (see 1990 Millipore catalog pp. 177–178, incorporated herein by reference); and likewise, the Selection By Catalysis-Accelerated Movement can employ such linker procedures. The success of this embodiment, without necessarily wishing to be bound by any one particular theory, may be related to the concentration of substrate on the membrane (mmol/cm$^2$) due to steric limitations and other factors typically considered by those skilled in the art. The substrate concentration on the membrane can be as in the Selection By Catalysis-Accelerated Movement embodiment. Thus, the concentration of the substrate on the membrane can be optimized without undue experimentation from this disclosure for any particular catalytic moiety-substrate system.

Those skilled in the art will understand that other solid-phase surfaces can be substituted for the membrane. For example, non-magnetic or magnetically responsive particles can be used as described above with respect to selection by catalysis accelerated movement.

D. Application of Phage, Virus, Cell or Moiety

The phage, virus, cell or moiety binds to the membrane according to established binding kinetics of antibodies to antigens (10). In accordance with these findings, the exposure time of a phage-, virus-, cell- or moiety- containing solution to the substrate-membrane can be at two minutes (rapid binders) and ten minutes (slow binders). After these times, the membrane is preferably substantially immediately and preferably quickly (for 1–10 preferably 1–5 seconds) given primary wash, either on the surface or by flow through. The wash is done to remove moieties, such as virus, phage or cell antibodies which bind weakly to substrate (e.g., extremely high apparent binding constant, $K_m$, antibodies) or those non-specifically bound to the membrane surface.

E. Incubation

The slightly moist membrane can then be incubated at 20°–40°, typically 25° or 37° C. in a humidified chamber for a suitable time such as 0.5 to 16 hours typically 1 hour, 3 hours, 6 hours, or 12 hours, depending on the particular moiety, e.g., antibody. A secondary wash is then carried out for a suitable time typically 1–5 seconds in a chosen buffer (usually the same as the reaction buffer). More than one secondary wash to remove catalysts can be done, although one wash is preferred as it is much less labor intensive. The secondary wash(es) can be done either on the surface of the membrane or by .flowing buffer through the membrane.

F. Use of the Secondary Wash

The secondary wash(es) containing the catalytic phages, viruses, cells or moieties can be concentrated and prepared for catalytic use or for infection of a suitable host e.g., *E. coli* with the phages, or for generation of catalysts by cells, e.g., causing recombinant virus infected cells to undergo a lytic cycle. This membrane technique embodiment of the invention can be repeated with the secondary wash(es) to reduce the amount of any non-catalytic phages, viruses, or cells (or antibody therefrom) or of non-catalytic moieties which may have been included in the secondary wash(es) and to further enrich the concentration of. catalytic moieties. Host, e.g., *E. coli*, colonies containing phage clones enriched for catalytic activity can be grown to secrete sufficient catalyst, e.g., catalytic antibody or catalytic fragment thereof to be purified and screened or used directly for catalytic activity. Purification of resultant catalysts, e.g., catalytic antibodies, can then be by standard procedures.

IV. Selection By Changes In Binding as a Function of Reaction Condition Such as Temperature or Competition A. Overview Regarding Temperature The effects of temperature on binding and catalysis differ for a given protein catalyst. Thus, as temperature increases from one temperature such as a low or rather cold temperature at which there is binding but very little catalysis to a second, generally higher temperature at which there is substantial catalysis, the apparent dissociation constant of the catalyst and its substrate will change in a discontinuous fashion. This change in apparent substrate binding of catalyst (but not a non-catalyst) with temperature change forms a basis for an embodiment of the invention for the separation, selection or concentration of catalytic moieties or of phages, viruses or cells capable of expressing a catalytic moiety such as a catalytic antibody or catalytic portion thereof from a large pool of non-catalytic moieties, phages, viruses or cells.

B. The Effect of Temperature on Binding and Catalysis

Binding is subject to the following physical observations and phenomena:

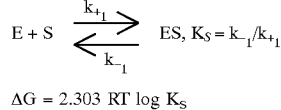

$$\Delta G = 2.303 \, RT \log K_S$$

where E is a catalyst, such as an enzyme or antibody, S is a substrate, ES is the Catalyst-Substrate complex (which can go to product, P), G is Gibbs free energy, R is universal gas constant, and T is the temperature (in Kelvin).

Thus, a plot of $T^{-1}$ vs. log $K_s$ for a binding molecule such as an enzyme at low temperature or a non-catalytic antibody will give a straight line with a slope of $(2.303R)/\Delta G$.

For a catalyst such as an enzyme or catalytic antibody, the apparent binding constant is not $K_s$ but $K_m$. For the simple reaction shown:

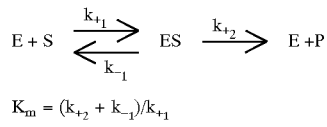

The effect of temperature on $k_{-1}/k_{+1}$ ($K_s$) was discussed above. The effect of temperature $k_{+2}$ is determined using the Eyring theory of absolute reaction rates. The effect of temperature on the reaction ($k_{+2}$) is $$\log k_{+2} = [-(\Delta H^* + RT)/2.303] \times T^{-1}$$

(where $\Delta H^*$ is the enthalpy of activation), so a plot of log $k_{+2}$ (log $V_{max}$) vs. $1/T$ gives a slope of $-(\Delta H^* + RT/2.303)$.

Thus, the effect of temperature on $K_m$ depends on the relative sizes of $k_{+2}$ and $k_{-1}$; the extreme cases being that $K_m = k_{+2}/k_{-1}$ and $K_m = K_s$. In most cases however, $K_m$ equals some mixture of rate constants ($K_m = (k_{+2} + k_{-1})/k_{+1}$).

Combining the above concepts and observations, binding moieties such as antibodies have a linear relationship between $1/T$ and $K_s$ since only one temperature coefficient is involved, whereas with catalytic moieties (such as an enzyme, catalytic antibody or catalytic portion thereof) the apparent binding constant ($K_m$) depends on two (or more) temperature-dependant phenomena, binding and catalysis, each having its own temperature coefficient. Catalysis introduces into the enthalpic term in the equation above, a factor that is temperature dependent. Therefore, in the case of a catalytic moiety, the relationship between $1/T$ and $K_m$ is not linear, but is curved depending on the differences in catalysis and binding temperature coefficients. This embodiment of the invention exploits the effects of temperature on apparent binding to isolate, select, screen or increase the concentration of catalytic moieties, such as viruses, phages or cells capable of expressing a catalytic moiety such as a catalytic antibody or catalytic portion thereof.

C. The Procedures, In General For Separation Based on Temperature

In general, in this embodiment a method is provided to separate phages, cells or moieties based on the effect of temperature on apparent substrate binding. Those that are catalytic respond differently to temperature changes than those that are non-catalytic. Moieties such as viruses, phage or cell antibodies having similar $K_s$ values at low temperatures (where catalysis substantially does not occur) will have similar temperature dependencies of their $K_s$ values. This is valid for the vast majority of moieties, e.g., viruses, phages or cells having similar $K_s$ values. In practice:

1. Moieties, e.g., viruses that bind hapten are separated on a column of immobilized substrate at a first, generally low temperature (e.g., −30° to 0° C., typically −20° C., for example); those phages that bind loosely (having high $K_s$) elute first and those phages binding tightly (having low $K_s$) elute later.
2. Fractions are collected.
3. At a second, generally higher temperature (e.g., +20° to 45° C., typically +25° or +37° C., for example), individual concentrated fractions are re-eluted on the same column and fractions once again be collected from each elution.
4. The fraction or fractions eluting containing the highest concentration of viruses, phages, cells or moieties are detected directly by absorbance or indirectly by Western blot, or in the case of phages following infection of a host such as *E. coli* with an aliquot of each fraction. Viruses, phages, cells or moieties eluting in fractions other than the main fraction(s) have different temperature coefficients than the viruses, phages, cells or moieties (non-catalytic) eluting in the main fraction. Since they elute with different affinities from the bulk (noncatalytic) viruses, phages, cells or moieties, the fractions eluting outside of the main fraction(s) can then be further enriched or concentrated. The reason is that the viruses, phages, cells or moieties eluting outside the bulk fraction(s) have, in addition to a temperature coefficient for binding, a temperature coefficient for catalysis. In general, the effect of temperature on the apparent binding constant of catalytic viruses, phages, cells or moieties differ substantially from the bulk of non-catalytic viruses, phages, cells or moieties.
5. Enriched rare viruses or phages are then used to infect a host such as *E. coli* and isolated moieties, therefrom, e.g., antibodies obtained are used for catalysis or are further screened for catalytic activity. Likewise, enriched cells are isolated and used to express the catalytic moiety or are induced to undergo a lytic cycle to produce a virus or phage generation. similarly, enriched moieties isolated by the procedure are used for catalysis.

The above details of this embodiment of the invention can vary depending upon the moiety and may involve substrate immobilized in a column matrix by standard methods (gravity or pump separation), on a electrophoresis gel (electric field separation), in a centrifuge tube (g-force separation), for instance a centrifuge tube containing immobilized substrate suspended in a viscous solution, or other basic ways of separating viruses, phages, cells or moieties through suspended or immobilized substrate. The low temperature separation is preferably carried out in aqueous media, with the temperature kept low by refrigeration, dry ice, or liquid nitrogen or liquid helium. The aqueous medium is kept from freezing by inclusion of suitable concentrations of NaCl or another salt or with glycerol. And, this embodiment can be repeated so as to further concentrate a sample of catalytic moieties, viruses, phages or cells.

D. Overview Of Selection By Competition With Non-Reactive Substrate Analog

This embodiment employs an analog of the substrate in the catalytic reaction of interest. In the analog, the target bond is resistant to alteration by the catalytic species; but the analog has sufficient structural similarity to exhibit similar binding affinity as the substrate molecule to the moiety, whether it be catalytic or non-catalytic. An example of this for an esterolytic reaction of the $R^3COOR^4$ ester substrate is the structure $R^3COCH_2R^4$ which sufficiently mimics the ester structure, but the $C(=O)CH_2$ target bond while structurally similar to the ester is resistant to alteration by the esterolytic catalyst. A number of such nonreactive substrate analogs exist for any particular reaction and the selection of the appropriate analog for use can be determined by the skilled artisan from this disclosure without undue experimentation, taking into consideration the structural similarity between the potential nonreactive substrate analog and the substrate itself, the resistance to alteration of the target bond in the analog, the chemical reaction involved, the binding affinity of the analog and other factors within the ambit of the skilled artisan.

Thus, this embodiment provides for separation or concentration of catalytic phages, viruses or cells or catalytic moieties by contacting a sample thereof with a non-reactive substrate analog, preferably an immobilized analog such as an analog coupled to a solid phase support packed in a column. The contacting is preferably in the presence of such an analog (mobile). From this contacting fractions are collected. Individually, fractions are again contacted with the immobilized non-reactive substrate, but in the presence of substrate. Fractions are again collected. Catalytic phages, viruses or cells or catalytic moieties dissociate from the substrate at a different rate than their non-catalytic counterparts such that if the analog is coupled to a solid phase support packed in a column, the catalysts elute outside of the main fraction, i.e., the catalysts elute either before or after the main fraction.

In particular, virus, phage, cell or moiety in the sample which has sufficient catalytic activity (Ab) such that $k_2 > k_{-1}$ in the reaction equilibrium equation (wherein "S" is substrate and "P" is product):

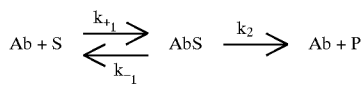

elute in the second elution with retention times different than for the main peak of phages, viruses, cells or moieties eluting as the catalysts dissociate at different rates from the AbS complex than their non-catalytic counterparts. Collection of viruses, phages, cells or moieties outside of the main peak will therefore enrich for (increase concentration of) or select for those exhibiting catalytic activity. Depending on the particular catalytic mechanism, catalysts elute in the second elution later or sooner than the main peak (15) see also FIGS. 1 and 2; however, from this disclosure the skilled artisan can determine whether the catalysts are eluting sooner or later than the main fraction, without undue experimentation; for instance by determining whether that which elutes outside of the main peak is eluting before or after the main peak, and by considering the turnover number achieved by that which elutes outside of (before or after) the main peak, and by taking into consideration other factors within the ambit of the skilled artisan. The noncatalyst association/dissociation with substrate (or non-reactive substrate analog) is expressed as $K_s$:

$$K_s = k_{-1}/k_{+1}$$

because the noncatalyst (Nc) associates and dissociates with substrate or nonreactive substrate (S*) only as follows:

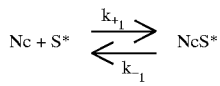

In the catalytic mechanism shown in the above scheme (with no catalytic intermediates occurring between the Michaelis complex (AbS) and product formation, P), the apparent association/dissociation of antibody and substrate can be written as $K_m$:

$$K_m = (k_2 + k_{-1})/k_{+1}.$$

Under these circumstances the value of $K_s$ must always be less than that for $K_m$; i.e., the non-catalytic viruses, phages, cells or moieties bind substrate more tightly and hence elute later in the second elution than catalytic viruses, phages, cells or moieties (see FIG. 1).

On the other hand, if the catalytic viruses, phages, cells or moieties (Ab) follow mechanisms in which reaction intermediates (such as covalent intermediates) occur on the reaction coordinate between the Michaelis complex and product formation, such as shown here in the mechanism below (wherein "S" is substrate, "AbS$_2$" is the intermediate, and "P" is product):

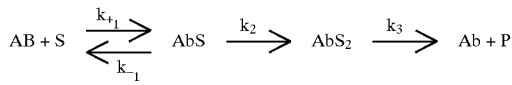

the term describing the apparent association/dissociation of substrate is different in this equation wherein $K_m$ has a value that is less than that of $K_s$, namely:

$$K_m = [K_s] [k_3/(k_2+k_3)].$$

Thus, for this mechanism or any mechanism in which intermediates occur after the AbS complex, the catalytic viruses, phages, cells or moieties bind tighter and elute later in the second elution than the non-catalysts (see FIG. 1).

Figure 2:
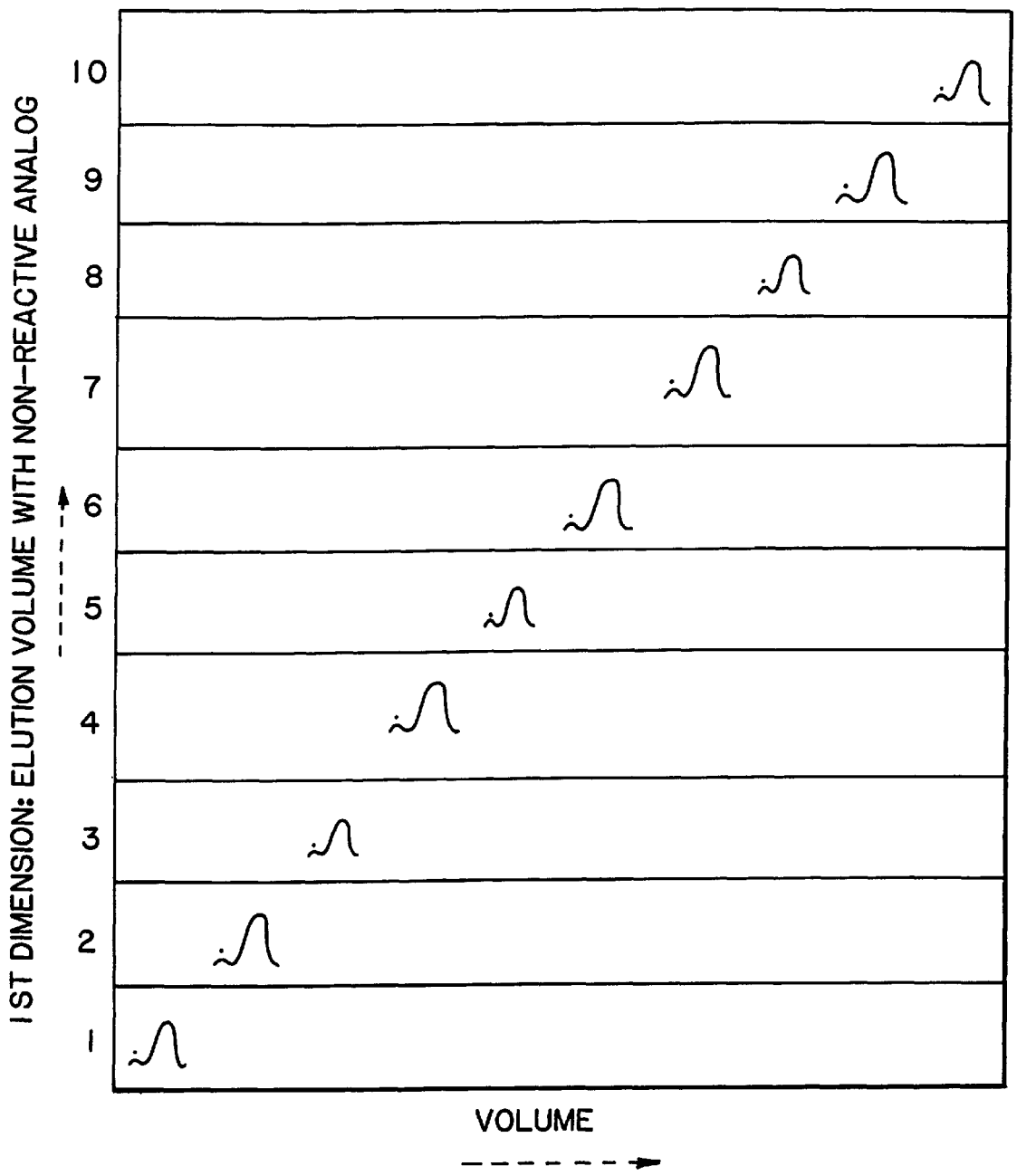

However, if the reaction of AbS→Ab+P is very rapid such as to cause $K_s$ to be greater than $K_m$, or, if $K_s$ for the NcS complex is greater than $K_m$, then the catalysts will elute sooner than the non-catalysts, as shown in FIG. 2. Thus, collecting those. moieties, cells, viruses or phages which exhibit different binding, e.g., elute later or sooner, will not only be the isolation catalysts, but will also be the isolation of the best catalysts in the sample.

E. Particulars of Selection By Competition With Non-Reactive Analog

The non-reactive substrate analog is preferably coupled to a solid phase support to allow the preparation of an affinity matrix which is preferably packed into a chromatography column. A suspension of viruses, phages, cells or moieties potentially including those which act catalytically, e.g., phages, viruses or cells expressing a catalytic antibody or catalytic portion thereof which bind to a transition state analog used to generate the immune response which elicited the antibody and the expression thereof, is applied to the column under conditions such as temperature, buffer composition, flow rate, which allow the viruses, phages, cells or moieties with an affinity for the substrate analog to bind to the immobilized ligand such that they are retained on the column relative to those with no affinity for the ligand. The viruses, phages, cells or moieties eluting from the column at successive time intervals are collected, pooled into appropriate fractions, and concentrated. Inclusion of soluble non-reactive substrate analog in the buffer used for the elution causes the binders in the sample to elute earlier in the column profile by competing with the solid phase ligand for binding to the viruses, phages, cells or moieties. Similarly, inclusion of the substrate in the eluting buffer has an identical effect on the elution of non-catalysts which bind to substrate with a similar $K_s$ as they bind with the non-reactive substrate analog. Thus, fractions eluted with the non-reactive substrate analog from the non-reactive substrate analog column are then again passed on the column, but in the presence of substrate, preferably at equal or lower concentration than that at which the analog was used to achieve elution.

In the case of catalytic moieties, viruses, phages or cells, however the substrate will be either less or more effective at accelerating their elution from the column because substrate is converted to product(s) by the catalysts which are released from the binding site, allowing the catalysts to re-bind to the immobilized ligand. Thus catalysts elute later or earlier from a column eluted with substrate than they will from the same column eluted with non-reactive substrate analog. This forms the basis of the two dimensional separation profiles shown in FIGS. 1 and 2. In FIGS. 1 and 2 the first dimension elution with non-reactive substrate analog from the non-reactive substrate analog column is portrayed in the vertical direction and the second dimension elution with substrate from the non-reactive substrate analog column is portrayed in the horizontal direction. The starred peaks represent fraction(s) eluting outside of the main fraction. The starred peaks are normalized as shown in FIGS. 1 and 2 as the catalysts can elute as a trailing edge following the main peak (FIG. 1) or as a trailing edge preceding the main peak (FIG. 2), i.e., the catalysts elute significantly later or earlier than the main peak(s) and are thus pooled to collect or concentrate the catalytically enriched population. FIG. 1 shows the profile for $K_m > K_s$ (catalysts binding longer than non-catalysts), and FIG. 2 shows the profile for $K_s > K_m$ (catalysts eluting sooner than non-catalysts).

With respect to the hydrolysis of ester (II) (discussed above);

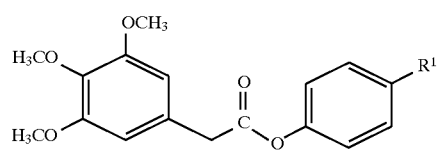

which ester can be generally shown by the following formula (XXXI)

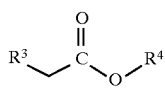

wherein R³ is

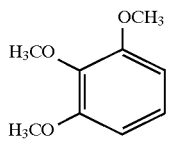

and R⁴ is

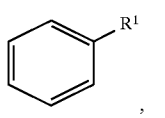

, the following act as a non-reactive substrate analog:

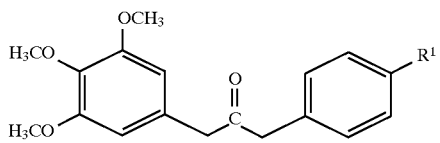 XXI

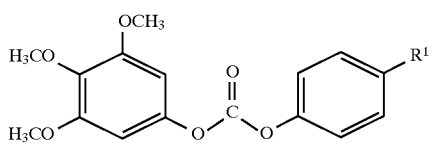 XXII

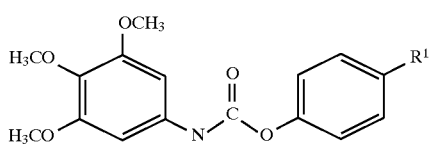 XXIII

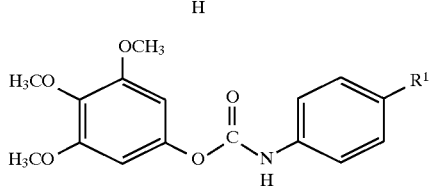 XXIV

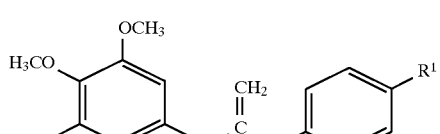 XXV

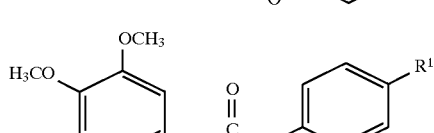 XXVI

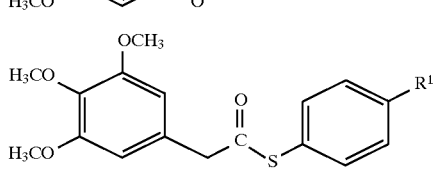 XVII

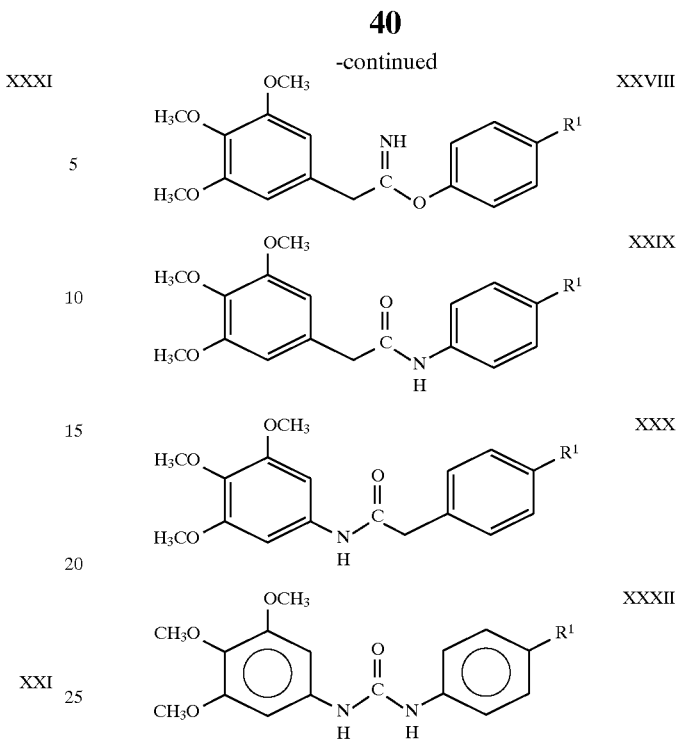

Thus, as shown herein, a non-reactive substrate analog for an ester can be a ketone, carbonate, carbamate, ether such as a methylene ether, a reversed ester, thio ester, imino ester, amide and reversed amide having the same or similar substituents (e.g., R³ and R⁴) as the substrate ester. Of course, from this disclosure the skilled artisan can devise non-reactive analogs for other substrates without undue experimentation. Moreover, non-reactive analogs can be devised for reactions other than esterase reactions including peptide hydrolysis, oxidation/reduction, addition, elimination, condensation, isomerization, and transfer reactions. Particularly since as shown herein a non-reactive analog is structurally similar to the substrate, e.g., same or similar substituent groups, but, the bond at the reaction site of the substrate is different so as to resist alteration (reaction) by the catalyst but is similar to the target bond nonetheless. For instance, if the target bond is a bond selected from ester such as typical ester, reversed ester, thio ester, or imino ester, ketone, carbonate, carbamate, ether such as typical ether or methylene ether, and amide such as typical amide, reversed amide and amino, the bond at the reactive site of the non-reactive analog is preferably another member selected from that group.

This embodiment can include further alternative embodiments. For instance, the coupling density of the ligand to the solid phase, the nature of the solid phase support, buffer composition, flow rate and concentration of eluting species can be, from this disclosure, varied to achieve optimal selectivity (concentration or isolation of best catalysts) without undue experimentation, especially in view of the equations above. In addition, given the above equations, and the thrust of this embodiment for there to be competition in binding so that catalysts bind differently due to catalytic behavior and therefore elute differently, this embodiment and this disclosure thereof allows the skilled artisan, without undue experimentation, to select as compounds for the solid phase ligand(s) and eluting species not only the above-described non-reactive analog and substrate, but also other compounds such as transition state analog(s) and even unrelated compound(s) with significant affinity for binding to the moiety of interest. It is noted that Selection By Changes in Binding By Competition not only allows for isolation or concentration of catalysts; but, by the teachings herein, allows for separation of the better catalysts, especially since the selection is based upon and directly correlated to catalysis ($K_m$).

In a further alternative of this embodiment of the invention, the non-reactive analog is attached to a two-dimensional support, such as a membrane as described above, and, the sample is driven across the membrane surface by forces other than gravity (which is used in the column). For example, the sample can be driven across the non-reactive-analog membrane (preferably moistened) by an electric field, i.e., the separation of catalysts and non-catalysts is electrophoretically induced. In this instance, the catalysts are again found in the minority fraction. The conditions for electrophoresis induced separation are empirically determined by the skilled artisan without undue experimentation by taking into account typical factors, as discussed above, so that there is an optimum between the charge on the sample undergoing separation and minimum conductivity of the medium (non-bound matter on membrane surface such as the moistening solution thereon), as this promotes maximum separation by charge.

Of course, a catalytic population or sample (sometimes herein called a "subpopulation" or "second population") of viruses, phages, cells or moieties can be obtained by one method of this invention and either it or its next generation (such as from host infection or from inducing a lytic cycle) can be further selected or concentrated by another method of this invention. For instance, the secondary wash(es) (subpopulation or second subpopulation) from Catalytic Selection By Surface Binding can then be subjected to Selection By Catalysis-Accelerated Movement, Selection By Changes in Enthalpic Component of Binding as a Function of Temperature, Selection By Changes in Binding By Competition, or Mechanism-Based Inhibitor Selection.

Likewise, the scrapings (subpopulation or second subpopulation) from Selection By Catalysis-Accelerated Movement can then be subjected to Selection By Surface Binding, Selection By Changes in Enthalpic Component of Binding as a Function of Temperature, Selection By Changes in Binding By Competition, or Mechanism-Based Inhibitor Selection. Similarly, the sample(s) exhibiting a different effect of temperature on apparent binding in Selection By Changes in Enthalpic Component of Binding as a Function of Temperature (e.g., those that elute or bind outside of main fraction(s)) can then be subjected to Selection By Surface Binding, Selection By Catalysis-Accelerated Movement, Selection By Changes in Binding By Competition, or Mechanism-Based Inhibitor Selection. And, the sample(s) exhibiting different binding when contacted with immobilized non-reactive substrate analog in the presence of substrate (e.g., those that elute or bind outside of main fraction(s)) can then be subjected to Selection By Surface Binding, Selection By Catalysis-Accelerated Movement, Selection By Changes in Enthalpic Component as a Function of Temperature, or Mechanism-Based Inhibitor Selection.

The inhibitors, substrates and non-reactive substrate analogs discussed herein can be synthesized by the skilled artisan, without undue experimentation, by following teachings in the art (see, e.g., 33).

The following non-limited Examples are given by way of illustration and are not to be considered a limitation of this invention, many apparent variations of which are possible without departing from the spirit or scope thereof. In all cases these include reactions other than ester hydrolysis reactions, such as peptide hydrolysis, oxidation/reduction, addition, elimination, condensation, isomerization, and transfer reactions.

EXAMPLES

Example 1

Construction of Recombinant Phase Library

Generation of a library of VH and VL antibody domains for expression on the surface of fd and M13 phages is accomplished using PCR technology and appropriately designed consensus primers (1,2,3,4,11; see also PCT Publication WO920 1047 published Jan. 23, 1992 incorporated herein by reference). The starting material for PCR is spleen RNA obtained from a mouse, immunized with hapten (I). A set of PCR consensus primers for amplification of mouse antibody variable domains is shown below and is also as previously described (2), wherein SEQ A is provided to show partial alignment of the primer sequence (SEQ ID NO: 1) and with coding for the VH domain (SEQ ID NO: 2).

```
5'end-    5'AGGTGAAACTGCAGGAGTCAGG 3'              SEQ ID NO: 1
            CC  G         C     T                   SEQ A 3'end-    5'TGAGGAGACGGTGACCGTGGTCCCTTGGCCCC 3'     SEQ ID NO: 2

VL
5'end-    5'GACATTGAGFCTCACCCAGTCTCCA3'              SEQ ID NO: 3

3'end-    5'CCGTTTGATTTCCAGCTTGGTGCC 3'
            CCGTTTTATTTTCCAGCTTGGTCCC
            CCGTTTTATTTCCAACTTTGTCCC
            CCGTTTCAGCTCCAGCTTGGTCCC                 SEQ ID NO: 4
```

Following amplification of VH and VL domains a second PCR reaction is used to link the domains together by a short peptide to produce single chain Fv. Linking peptide, PCR primers and protocol are as previously described (2). Finally, a third PCR reaction is used to incorporate appropriate restriction enzyme sites at the 5' and 3' end of the single chain Fv library to allow cloning into a phage display expression vector such as fdDOG1 for fd surface display (2) or pComb3 for M13 surface display (11).

Alternatively, a variable domain library can also be obtained from a nonimmunized mouse or other mammal such as a human. The starting material in this instance is RNA from spleen (mouse or other mammal) or lymphocytes (human). Amplification and cloning is performed as described above except in the case of the human library the sequences of PCR consensus primers are modified to reflect differences between mouse and human variable domains.

Human consensus primers and construction of a human antibody phage display library is as has been previously described. (18)

Furthermore, the expression of Fab (as opposed to scFv) on the phage surface, so that the phage library includes a Fab library, is accomplished using a different set of 3' PCR primers than those above so as to amplify those portions of the heavy and light constant region containing cysteine residues involved in formation of disulfide bonds between the two chains; this is accomplished as previously described (4). Vectors for phage surface display of a Fab library include pHenI for fd phage (19) and pComb3 (11) and pTacCP (20) for M13.

Using these techniques, recombinant phages expressing a catalytic antibody or catalytic portion thereof elicited by hapten I for the ester hydrolysis of substrate II are generated from fd and M13 phages; the initial population of the recombinant phages is herein called cat1fd and cat1M13, respectively.

Example 2

Mechanism-Based Inhibitor Selection

A solution containing cat1fd is passed over an affinity column (Sepharose) containing compound of formula I as the bound hapten (linkage through R). A first subpopulation of phages (cat1fd1) that bind to the hapten are collected by subsequently passing free hapten over the column followed by dialysis of phages eluted by the free hapten wash so as to remove bound hapten. This first subpopulation (cat1fd1) is tested for its ability to catalyze the hydrolysis of the compound of formula II ($R^1$=$NO_2$) by determining the rate enhancement factor (pH 7.0, 50 mM Hepes, 150 mN NaCl, 30° C., 0.5–3 hrs.); the first subpopulation shows a low amount of catalytic activity.

A first portion of the first subpopulation (cat1fd1) is contacted with compound of formula III (no $R^s$ linkage) under the reaction conditions for hydrolysis of compound of formula II (pH 7.0, 50 mN Hepes, 150 mM NaCl, 30° C. 0.5–3 hrs.). This first portion is then passed over the hapten affinity column, and phages which in this pass do not bind to the column are collected and used to infect *E. coli*. The resultant phages from the *E. coli* infection (cat1fd2) are tested (rate enhancement) for the ability to catalyze the hydrolysis of compound of formula II ($R^1$=$NO_2$) (pH 7.0, 50 mM Hepes, 150 mM NaCl, 30° C., 0.5–3 hrs.); cat1fd2 show greater catalytic activity (turnover number) than the first subpopulation (cat1fd1).

A second portion of the first subpopulation (cat1fd1) is contacted with compound of formula IV (no $R^s$ linkage, x=Br) under the reaction conditions for hydrolysis of compound of formula II. This second portion is then also passed over the hapten affinity column, and phages which in this pass do not bind to the column are collected and used to infect *E. coli*. The resultant phages from *E. coli* infection (cat1fd3) are tested (rate enhancement) for the ability to catalyze the hydrolysis of compound of formula II ($R^1$=$NO_2$) (pH 7.0, 50 mM Hepes, 150 mM NaCl, 30° C., 0.5–3 hrs.); cat1fd3 show greater catalytic activity (turnover number) than the first subpopulation (cat1fd1).

Example 3

Mechanism-Based Inhibitor Selection

Using the procedure of Example 2, third through tenth portions of the first subpopulation (cat1fd1) are each respectively contacted with compound of formula V through XI (no $R^s$ linkage, x=Br) under the reaction conditions for the hydrolysis of compound of formula II. Each of the third through tenth portions is then passed over the hapten affinity column (hapten I linkage through R) and those which do not bind are collected and used to infect *E. coli*. The resultant phages from *E. coli* infection (cat1fd4 through cat1fd10) are each tested (rate enhancement) for the ability to catalyze the hydrolysis of compound of formula II ($R^1$=$NO_2$) (pH 7.0, 50 mM Hepes, 150 mM NaCl, 30° C., 0.5–3 hrs.); each of cat1fd4 through cat1fd10 show greater catalytic activity (turnover number) than the first subpopulation (cat1fd1).

Example 4

Mechanism-Based Inhibitor Selection

Using the procedure as in Example 2, a first subpopulation, cat1M131, is isolated from cat1M13 by hapten affinity chromatography. By determining rate enhancement, cat1M131 shows a low amount of catalytic activity in the hydrolysis of compound of formula II.

A first portion of cat1M131 is contacted with compound of formula III (no $R^s$ linkage) under the reaction conditions for hydrolysis of compound of formula II. This first portion is then passed over the hapten affinity column and phages which in this pass do not bind to the column are collected and used to infect *E. coli*. The resultant phages from *E. coli* infection, cat1M132, are tested (rate enhancement) for the ability to catalyze the hydrolysis of compound of formula II ($R^1$=$NO_2$) (pH 7.0, 50 mM Hepes, 150 mM NaCl, 30° C., 0.5–3 hrs.); cat1M132 show greater catalytic activity (turnover number) than cat1M131.

A second portion of cat1M131 is contacted with compound of formula IV (no $R^s$ linkage, x=Br) under the reaction conditions for hydrolysis of compound formula II. This second portion is then passed over the hapten affinity column and phages which do not bind in this pass are collected and used to infect *E. coli*. The resultant phages from *E. coli* infection, cat1M133, are tested (rate enhancement) for the ability to catalyze the hydrolysis of compound of formula II ($R^1$=$NO_2$) (pH 7.0, 50 mM Hepes, 150 mM NaCl, 30° C., 0.5–3 hrs.); cat1M133 show greater catalytic activity (turnover number) than cat1M131.

Example 5

Mechanism-Based Inhibitor Selection

Using the procedure of Example 4, third through tenth portions of the first subpopulation (cat1M131) are each respectively contacted with compound of formula V through XI (no $R^s$ linkage, x=Br) under the reaction conditions for the hydrolysis of compound of formula II. Each of the third through tenth portions is then passed over the hapten affinity column (hapten I, linkage through R) and those which do not bind are collected and used to infect *E. coli*. The resultant phages form *E. coli* infection (cat1M134 through cat1M1310) are each tested (rate enhancement) for the ability to catalyze the hydrolysis of compound of formula II ($R^1$=$NO_2$) (pH 7.0, 50 mM Hepes, 150 mM Nacl, 30° C., 0.5–3 hrs.); each of cat1M134 through cat1M1310 show greater catalytic activity (turnover number) than the first subpopulation (cat1M131).

Example 6

Selection By Catalysis-Accelerated Movement

A portion of the first subpopulation cat1fd1 from Example 2 is mixed with bromphenol blue to make a phage paste.

Compound of formula II ($R^1=NO_2$) is supported on Immobilon AV membrane (through $R^1$). A very fine line of phage paste is streaked across the compound of formula II-Immobilon AV membrane. The membrane is incubated in a moist (50–100% relative humidity) environment at 25° C. for 48 hours. After incubation, with the assistance of a microscope, a razor is used to scrape and collect phages 0.10 mm from the original line. The collected phages, cat1fd11, are tested (rate enhancement) for the ability to catalyze the hydrolysis of compound of formula II ($R^1=NO_2$) (pH 7.0, 50 mM Hepes, 150 mM NaCl, 30° C. 0.5–3 hrs.); cat1fd11 show greater catalytic (turnover number) activity than cat1fd1.

Example 7

Selection By Catalysis-Accelerated Movement

Using the procedure in Example 6, the first subpopulation from Example 4, cat1M131, is mixed with bromphenol blue to make a paste and a very fine line of the paste is streaked across a compound of formula II-Immobilon AV membrane. After incubation (50–100% rh, 25° C., 48 hrs.), with vision aided by a microscope, a razor is used to scrape and collect phages 0.10 mm from the original line. The collected phages, cat1M1311, are tested (rate enhancement) for the ability to catalyze the hydrolysis of compound of formula II ($R^1=NO_2$) (pH 7.0, 50 mM Hepes, 150 mM NaCl, 30° C., 0.5–3 hrs.); cat1M1311 show greater catalytic activity (turnover number) than cat1M131.

Example 8

Selection By Surface Binding

A portion of the first subpopulation cat1fd1 from Example 2 is added as a solution to a formula II-Immobilon AV membrane (Example 6) and after two minutes and ten minutes the membrane is quickly washed (1–5 seconds) with buffer (same as solution). These washes are to remove any phages which are. weakly binding or non-binding to the substrate, and are thus discarded. The moist membrane is incubated (25° C., rh 50–100%) for 12 hours with a quick 1–5 second wash (with buffer same as solution) at 1 hour, 3 hours, 6 hours and 12 hours; these washes are collected, concentrated, and used to infect $E.$ $coli$. The resultant phages from $E.$ $coli$ infection, cat1fd12 are tested (rate enhancement) for the ability to catalyze the hydrolysis of compound of formula II ($R^1=NO_2$) (pH 7.0, 50 mM Hepes, 150 mM NaCl, 30° C., 0.5–3 hrs.); cat1fd12 show greater catalytic activity (turnover number) than cat1fd1.

Example 9

Selection By Surface Binding

A portion of the first subpopulation, cat1M31, from Example 4 is added as a solution to a formula II-Immobilon AV membrane (Example 6) and after two minutes and ten minutes the membrane is quickly washed (1–5 seconds) with buffer (same as solution). These washes are discarded. The moist membrane is incubated (25° C., rh 50–100%) for 12 hours with a quick 1–5 second wash (with buffer same as solution) at 1 hour, 3 hours, 6 hours and 12 hours; these washes are collected, concentrated, and used to infect $E.$ $coli$. The resultant phages from $E.$ $coli$ infection, cat1M1312, are tested (rate enhancement) for the ability to catalyze the hydrolysis of compound of formula II ($R^2=NO_2$) (pH 7.0, 50 mM Hepes, 150 mM NaCl, 30° C., 0.5–3 hrs.); cat1M1312 show greater catalytic activity (turnover number) than cat1M131.

Example 10

Selection By Changes in Enthalpic Component of Binding as a Function of Temperature Cat1fd as in Example 1 are passed over a column (Sepharose) of compound of formula II ($R^1=NO_2$, linkage through $R^1$) at −20° C. such that binding can occur, but not catalysis; and, fractions are collected. At 37° C. the fractions are again passed over the compound formula II column, with fractions again collected. Using absorbance, the fraction containing the lowest concentration of cat1fd (non-linear relationship between binding and temperature) is isolated and used to infect $E.$ $coli$. The resultant phages from $E.$ $coli$ infection, cat1fd13, are tested (rate enhancement) for the ability to catalyze the hydrolysis of compound of formula II ($R^1=NO_2$) (pH 7.0, 50 mM Hepes, 150 mM NaCl, 30° C., 0.5–3 hrs.); cat1fd13 show greater catalytic activity (turnover number) than cat1fd1.

Example 11

Selection By Changes in Enthalpic Component of Binding As A Function Of Temperature Cat1M13 as in Example 1 are passed over a column (Sepharose) of compound of formula II (as in Example 14) at −20° C. such that binding can occur, but not catalysis; and, fractions are collected. At 37° C. the fractions are again passed over the compound formula II column, with fractions again collected. Using absorbance, the fraction containing the lowest concentration of cat1fd (non-linear relationship between binding and temperature) is isolated and used to infect $E.$ $coli$. The resultant phages from $E.$ $coli$ infection, cat1M1313 are tested (rate enhancement) for the ability to catalyze the hydrolysis of compound of formula II ($R^1=NO_2$) (pH 7.0, 50 mM Hepes, 150 mM NaCl, 30° C., 0.5–3 hrs.); cat1M1313.

Example 12

Selection By Changes in Binding By Competition

Cat1fd as in Example 1 are passed over a column (Sepharose) of compound of formula XXI (linkage through $R^1$) and are eluted with a buffer solution containing compound of formula XXI. Fractions are collected and concentrated. These fractions are then individually applied to the same column and eluted with substrate (compound of formula II ($R^1=NO_2$). The two dimensional separation profile is as shown in normalized FIG. 1: The bulk of the phages eluting in the second pass over the column elute as a major peak with about the same retention as for the first pass over the column. The phages eluting later than the bulk are isolated and pooled and used to infect $E.$ $coli$. The resultant phages from $E.$ $coli$ infection, cat1fd 14 are tested (rate. enhancement) for the ability to catalyze the hydrolysis of compound of formula II ($R^1=NO_2$) (pH 7.0, 50 mM Hepes, 150 mM NaCl, 30° C., 0.5–3 hrs). Cat1fd14 show greater catalytic activity (turnover number) than cat1fd1.

Example 13

Selection By Changes In Binding Competition

Using the procedure of Example 12, additional portions of cat1fd are each respectively passed over a column. Each column is of compound of formula XXII through XXX and XXXII (linkage through $R^1$). Each portion is eluted with the respective non-reactive substrate analog linked to the column. Fractions from each elution are then individually applied to the same column from which they were eluted and this time eluted with substrate (compound of formula II, $R^1=NO_2$). The two dimensional separation profile for each is as shown in normalized FIG. 1. The later eluting phages from each elution are individually isolated and pooled and used to infect *E. coli*. The resultant phages from *E. coli* infection, cat1fd15 through cat1fd24, are tested (rate enhancement) for the ability to catalyze the hydrolysis of compound of formula II ($R^1=NO_2$) (pH 7.0, 50 mM Hepes, 150 mM NaCl, 30° C., 0.5–3hrs.); each of cat2fd15 through cat1fd24 show greater catalytic activity (turnover number) than cat1fd1.

Example 14

Selection By Changes In Binding By Competition

Cat1M13 as in Example 1 are passed over a column (Sepharose) of formula XXI (linkage through $R^1$) and are eluted with a buffer solution containing compound of formula XXI. Fractions are collected and concentrated. These fractions are then individually applied to the same column and eluted with substrate (compound of formula II, $R^1=NO_2$. The two dimensional separation profile is as shown in normalized FIG. 1: The bulk of the phages eluting in the second pass over the column elute as a major peak with about the same retention as for the first pass over the column. The phages eluting later than the bulk are isolated and pooled and used to infect *E. coli*. The resultant phages form *E. coli* infections, cat1M1314 are tested (rate enhancement) for the ability to catalyze the hydrolysis of compound of formula II ($R^1=NO_2$) (pH 7.0, 50 mM Hepes, 150 mM NaCl, 30° C., 0.5–3 hrs.); each of cat1M1314 show greater catalytic activity (turnover number) than cat1M131.

Example 15

Selection By Changes In Binding Competition

Using the procedure of Example 21, additional portions of cat1M13 are each respectively passed over a column. Each column is of compound of formula XXII through XXX and XXXII (linkage through $R^1$). Each portion is eluted with the respective non-reactive substrate analog linked to the column. Fractions from each elution are then individually applied to the same column from which they were eluted and this time eluted with substrate (compound of formula II, $R^1=NO_2$). The two dimensional separation profile for each is as shown in normalized FIG. 1. The later eluting phages from each elution are individually isolated and pooled and used to infect *E coli*. The resultant phages from *E. coli* infection, cat1M1315 through cat1M1323, are each tested (rate enhancement) for the ability to catalyze the hydrolysis of compound of formula II ($R^1=NO_2$) (pH 7.0, 50 mM Hepes, 150 mM NaCl, 30° C., 0.5–3 hrs.); each of cat1M1315 through cat1M1323 show greater catalytic activity (turnover number) than cat1M131.

Example 16

Construction of Phage Library

Using the procedures set forth in U.S. application Ser. No. 07/773,042, filed Oct. 10, 1991, mice are immunized with hapten IA or IB to elicit catalytic antibodies which catalyze the hydrolysis of compound IIA or IIB to yield 5-fluorouridine.

Employing the procedures of Example 1, spleen RNA from the immunized mice, PCR consensus primers for amplification, PCR to link domains by a, short peptide to produce single chain Fv, PCR to incorporate restriction enzyme sites at the 5' and 3' end of the single chain Fv library, and cloning into respective phage display vectors of fd, lambda and M13 are employed to produce recombinant phages expressing a catalytic antibody or catalytic portion thereof elicited by hapten IA or IB for the ester hydrolysis of substrate IIA or IIB; the initial population of these recombinant phages is herein called cat2fd, ca2λ and cat2M13 respectively.

Example 17

Mechanism-Based Inhibitor Selection: Generation of First Subpopulation

A solution containing cat2fd is passed over an affinity column (Sepharose) containing compound of formula IA as the bound hapten (linkage through $NH_2$). A first subpopulation of phages (cat2fd1A) that bind to the hapten are collected by subsequently passing free hapten over the column followed by dialysis of phages eluted by the free hapten wash so as to remove bound hapten. This first subpopulation (cat2fd1A) is tested for its ability to catalyze the hydrolysis of both compound of formula IIa and IIB by determining the rate enhancement factor (pH 7.0, 50 mM Hepes, 150 mM NaCl, 30° C., 0.5–3 hrs.); the first subpopulation shows some catalytic activity. This procedure is repeated with another solution containing cat2fd, but the bound hapten is compound of formula IB. The first subpopulation from the repeated procedure, cat2fd1B also shows some catalytic activity in the hydrolysis of both compound of formula IIA and IIB. Cat2fd1A and cat2fd1B are pooled for the first subpopulation, cat2fd1.

In the same fashion a first subpopulation from cat2M13, namely cat2M131, is generated. Cat2M131, as well as subsubpopulations from which they are generated (cat2M131A and cat2M131B) show some catalytic activity in the hydrolysis of both compound of formula IIA and IIB.

Example 18

Mechanism-Based Inhibitor Selection

A first portion of the first subpopulation cat2fd1 is contacted with compound of formula XII covalently linked to a Sepharose column, as described above, under the reaction conditions for hydrolysis of compound of formula IIA or IIB (pH 7.0, 50 mM Hepes, 150 mM NaCl, 30° C., 0.5–3 hrs.). That which elutes is collected and discarded. Mild inorganic acid (HCl) solution pH4–5) is passed over the column,and the DNA thereby eluted is used in *E. coli* transfection. The resultant phages from the *E. coli* transfection (cat2fd2) are tested (rate enhancement) for the ability to catalyze the hydrolysis of both compound of formula IIA and IIB (pH 7.0, 50 mM Hepes, 150 mM NaCl, 30° C., 0.5–3 hrs.); cat2fd2 show greater catalytic activity (turnover number) than the first subpopulation (cat2fd1).

Example 19

Mechanism-Based Inhibitor Selection

Following the procedure of Example 18, a second subpopulation, cat2M132 is generated from a portion of the first subpopulation cat2M131, and is tested for catalytic activity. Cat2M132 show greater catalytic activity than cat2M131.

Example 20

Mechanism-Based Inhibitor Selection

Following the procedure of Example 18, except that compound of formula XIII through XX are linked to the column, second subpopulations cat2fd3 through cat2fd10, respectively (from use of compound of formula XIII-XX) are generated from portions of the first subpopulation cat2fd1, and are tested for catalytic activity. Each of cat2fd3 through cat2fd10 show greater catalytic activity than cat2fd1.

Example 21

Mechanism-Based Inhibitor Selection

Following the procedure of Example 20, second subpopulations cat2l33 through cat2M1310 are generated from portions of the first subpopulation cat2M131 through the use of compound of formula XIII-XX, respectively; and, the second subpopulations are tested for catalytic activity. Each of cat2M133 through cat2M1310 show greater catalytic activity than cat2M131.

The foregoing Examples demonstrate the surprising advantages of the embodiments of the present invention: Catalysts can be selected or concentrated from non-catalysts, and better catalysts are obtained.

REFERENCES

1. Sastry, L., et al., Cloning of the Immunological Repertoire in Escherichia coli for Generation of Monoclonal Antibodies: Construction of a Heavy Chain Variable Region-Specific cDNA Library, Proc. Natl. Acad. Sci., USA (1989) 86; 5728–32.
2. Clackson et al., Making Antibody Fragments Using Phage Display Libraries, Nature (1991), 352; 624–28.
3. McCafferty, J., et al., Phage Antibodies: Filamentous Phage Displaying Antibody Variable Domains, Nature (1990), 348; 552–554.
4. Huse, W. D., et al., Generation of a Large Combinatorial Library of the Immunoglobulin Repertoire in Phage Lambda, Science (1989), 246; 1275–81.
5. Silverman, R. B., Mechanism-Based Enzyme Inactivation: Chemistry and Enzymology, Vols. I and II, CRC Press (1988) Boca Raton, Fla.
6. Shokat, K. and Schultz, P. G. lectures at the Ciba Symposium on Catalytic Antibodies, Sep. 30–Oct. 3, 1990, London, England.
7. Henis, Y. I., et al., Mobility of Enzymes on Insoluble Substrates: The Beta-Amylase-Starch Gel System, Biopolymers (1988), 27; 123–138.
8. Katchalski-Katzir, E., et al., Enzyme Diffusion and Action on Soluble and Insoluble Substrate Biopolymers, Biopolymers (1985) 24; 257–277.
9. Richter, P. H. & Eiger, M., Diffusion Controlled Reaction Rates in Spheroidal Geometry, Application to Repressor-Operator Association and Membrane Bound Enzymes, Biophysical Chemistry (1974), 2; 255–263.
10. Nygren, H., Werthen, M., & Stenberg, M., Kinetics of Antibody Binding to Solid-Phase-Immobilized Antigen, J. Immunol. Meth. (1987), 101; 63–71.
11. Barbas, C. F. III et al. Assembly of Combinatorial Libraries on Phage Surfaces: The Gene III Site. Proc. Natl. Acad, Sci. USA (1991), 88; 7978–7982.
12. Dixon, M. & Webb E. C. Enzymes (1979) Academic Press, New York, pp. 169–181.
13. Goodenough, U. Genetics (2d Ed. 1978) Saunders College, Philadelphia, pp. 1578–68.
14. Shokat, K. M. and Schultz, P. G., Catalytic Antibodies (1991) Wiley, New York, pp 118–34.
15. A. Ferscht, Enzyme Structure and Mechanism, 2nd Ed., pp. 101–103, W.H. Freeman & Co. NY (1985).
16. Tang et al., Proc. Natl. Acad. Sci. (1991), 88; 8784–86.
17. Inman and Barnett (1989), "Protein Recognition of Immobilized Ligands," T. W. Hutchens Ed., A. R. Liss, NY pp. 35–44).
18. Marks et al., By-Passing Immunization. Human antibodies form V-gene Libraries Display on Phage, J.Mol. Biol. (1991), 222; 581–97.
19. Hoogenboom et al., Multi-subunit Proteins on the Surface of Filamentous Phage: Methodologies for Displaying Antibody (Fab) Heavy and Light Chains, Nucl. Acids Res. (1991) 19; 4133–37.
20. Chang et al., Expression of Antibody Fab Domains on Bacteriophage Surfaces, J. Immunol. (1991) 147; 3610–14.
21. Ostrove, S. in Methods in Enzymology, 182, (M. P. Deutscher, ed.) 1990, Academic Press, New York, pp 357–371.
22. Sundarum, P. V. & Eckstein, F. Theory and Practice in Affinity Techniques, 1978, Academic Press, New York.
23. Morgan, M. R. A. & Dean, P. D. G. in Theory and Practice in Affinity Techniques (Sundarum, P. V. & Eckstein, F., eds.) 1978, Academic Press, New York, pp 14–22.
24. Stellwagon, E. in Methods in Enzymology, 182, (M. P. Deutscher, ed.) 1990, Academic Press, New York, pp 343–357.
25. Ostrove, S. & Weiss, S. in Methods in Enzymology, 182, (M. P. Deutscher, ed.) 1990, Academic Press, New York, pp 371–379.
26. Haff, L. A. & Easterday, R. L. in Theory and Practice in Affinity Techniques (Sundarum, P. V. & Eckstein, F., eds.) 1978, Academic Press, New York, pp 24–44.
27. Smith, M. C., Furman, T. C., Ingolia, T. D., & Pidgeon, C. J. Biol. Chem. 263, (1988) pp 7211–7215.
28. Carlsson, J., Svenson, A., Ryden, L. in Solid Phase Methods in Protein Sequencing Analysis, (Previero, A. & Coletti-Previero, M. -A., ed.) 1977, Elsevier/North Holland Biomedical Press, pp 29–37.
29. Bonnafous, J. C., Dornand, J., Faver, J., Sizes, M., Boschetti, E., Mani, J. C., J. Immunol. Methods 58, (1988) pp 93–107.
30. Pierce ImmunoTechnology Catalog & Handbook, (1991), pp D-12–D-13, and references therein.
31. Skerra, A., et al., "Filter Selection of Antibody Fab Fragments Secreted From Individual Bacterial Colonies: Specific Detection of Antigen Binding With A Two-Membrane System" Analytical Biochemistry (1991), 196; 151–55.
32. McCafferty, J. et al., "Phage-Enzymes: Expressing And Affinity Chromatography Of Functional Alkaline Phosphatase On The Surface Of Bacteriophage," Protein Engineering, (1991), vol. 4, no. 8, pp 955–61.
33. Comprehensive Organic Chemistry D. Barton & W. D. Ollis eds., Vol. 1–6, Pergamon Press, NY (1979).

Having thus described in detail the preferred embodiments of the present invention, it is to be understood that the invention defined by the appended claims is not to be limited by particular details set forth in the above description as many apparent variations thereof are possible without departing from the spirit or scope of the present invention.

What is claimed is:

1. A method for selecting a population of viruses or organisms, wherein the members of said population are capable of expressing a surface-bound catalytic moiety, comprising:

contacting said population with a surface including a substrate of a desired catalytic reaction, wherein members of the population having binding affinity for the surface but not having catalytic activity will bind to the surface, and wherein members of the population having binding affinity for the surface and catalytic activity will bind and engage in catalysis;

washing said surface to remove therefrom members of the population having catalytic activity; and isolating members of the population having catalytic activity by collecting the wash.

2. The method of claim 1 wherein the selection for catalytic activity further comprises, after contacting said population with the surface, prior to washing the surface to remove therefrom members of the population having catalytic activity and after sufficient time from the contacting for both members of the population not having catalytic activity and members of the population having catalytic activity to bind to the substrate but less than the time from contacting for members of said population having catalytic activity to complete a catalytic reaction, washing said surface so as to remove any members of said population having low or no affinity to the substrate.

3. A method for increasing the ratio of catalytic moieties to non-catalytic moieties in a sample comprising a population of viruses or organisms, which comprises:

contacting a sample with a surface including a substrate of a desired catalytic reaction, wherein members of the population having binding affinity for the surface but not catalytic activity will bind to the surface, and wherein members of the population having binding affinity for the surface and catalytic activity will bind to the surface and engage in catalysis; and washing said surface to remove therefrom members of the population having catalytic activity by collecting the wash.

4. The method of claim 3 wherein the selection for catalytic activity further comprises, after contacting said sample with the surface, prior to washing the surface to remove therefrom moieties having catalytic activity and after sufficient time from the contacting for both moieties not having catalytic activity and moieties having catalytic activity to bind to the substrate but less than the time from contacting for moieties having catalytic activity to complete a catalytic reaction, washing said surface so as to remove any portion of said sample having low or no affinity to the substrate.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGGTGAAACT GCAGGAGTCA GG                                            22

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TGAGGAGACG GTGACCGTGG TCCCTTGGCC CC                          32

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GACATTGAGC TCACCCAGTC TCCA                                      24

( 2 ) INFORMATION FOR SEQ ID NO:4:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCGTTTGATT TCCAGCTTGG TGCCCGTTT TATTTCCAG CTTGGTCCCC CGTTTTATTT      60

CCAACTTTGT CCCCGTTTC AGCTCCAGCT TGGTCCC                                97